US005840860A

United States Patent [19]

Annison et al.

[11] Patent Number: 5,840,860
[45] Date of Patent: Nov. 24, 1998

[54] FATTY ACID DELIVERY SYSTEM COMPRISING A HYDROLYZABLE BOND

[75] Inventors: Geoffrey Annison, The Concourse, Singapore; David L. Topping; Richard J. Illman, both of O'Halloran Hill, Australia

[73] Assignee: Commonwealth Scientific and Industrial Research Organization, Australia

[21] Appl. No.: 646,294

[22] PCT Filed: Nov. 17, 1994

[86] PCT No.: PCT/AU94/00713

§ 371 Date: Sep. 5, 1996

§ 102(e) Date: Sep. 5, 1996

[87] PCT Pub. No.: WO95/13801

PCT Pub. Date: May 26, 1995

[30] Foreign Application Priority Data

Nov. 17, 1993 [AU] Australia .................................. PM2454

[51] Int. Cl.⁶ ...................................................... C07H 1/00
[52] U.S. Cl. ......................... 536/1.11; 525/50; 525/54.2; 514/54; 436/71
[58] Field of Search ............................. 554/35; 564/215; 525/54.2, 50, 54.21, 54.24, 54.31, 54.4; 436/71; 514/23, 54, 57, 58, 59, 60, 61, 62; 536/1.11, 2

[56] References Cited

U.S. PATENT DOCUMENTS

| 5,039,703 | 8/1991 | Breuer ...................................... 514/557 |
| 5,260,279 | 11/1993 | Greenberg .................................. 514/21 |
| 5,444,054 | 8/1995 | Garleb et al. .............................. 514/54 |
| 5,505,966 | 4/1996 | Edman et al. ........................... 424/493 |

FOREIGN PATENT DOCUMENTS

| 50516/93 | 1/1994 | Australia . |
| 91/16881 | 11/1991 | WIPO . |
| 92/00732 | 1/1992 | WIPO . |

OTHER PUBLICATIONS

Englyst et al., "Classification and measurement of nutritionally important starch fractions", European Journal of Clinical Nutrition, 1992, pp. S33–S50.

Stephen, Alison M., "Starch and dietary fibre: their physiological and epidemiological interrlationships", Can. J. Physiol. Pharmacol, Feb. 1990, pp. 116–120.

Cummings et al., "The control and consequences of bacterial fermentation in the human colon", Journal of Applied Bacteriology, 1991, pp. 443–456.

Cassidy et al., "Starch intake and colorectal cancer risk: and international comparison", Br. J. Cancer, 1994, pp. 937–942.

Goodlad et al., "Large bowel fermentation in rats given diets containing raw peas (*Pisum sativum*)", British Journal of Nutrition, 1990, pp. 569–587.

Sakata, Takashi, "Effects of Indigestible Dietary Bulk and Short Chain Faty Acids on the Tissue Weight and Epithelial Cell Proliferation Rate of the Digestive Tract in Rate", J. Nutr.

Kvietys et al., "Effect of Volatile Faty Acids on Blood Flow and Osygen Uptake by the Dog Colon", Gastroenterology, 1981, pp. 962–969.

Cummings, J. H., "Short chain fatty acids in the human colon", Gut, 1981, pp. 763–779.

Smith, Paul J., "n–Butyrate alters chromatin accessibility to DNA repair enzymes", Carcinogenesis, 1986, pp. 423–429.

Kim et al., "Effect of sodium butyrate on three human colorectal adenocarcinoma cell lines in culture", Colonic Carcinogensis, pp. 317–323.

Weaver et al., "Short chain fatty acid distributions of enema samples from a digmoidoscopy population: an association of high acetate and low butyrate ratios with adenomatous polyps and colon cancer", Gut, 1988, pp. 1539–1543.

DeCosse et al., "Effect of Wheat Fiber and Vitamins C and E on Rectal Polyps in Patients With Familial Adenomatous Polyposis", Journal of the National Cencer Institute, Sep. 1989, pp.

Scheppach et al., "Effect of Butyrate Enemas on the Colonic Mucosa in Distal Ulcerative Colitis", Gastroenterology, 1992, pp. 51–56.

Groot et al., "Two–Year Feeding and Multigeneration Studies in Rats On Five Chemically Modified Starches", Fd. Chem. Toxic, 1974, pp. 651–663.

Til et al., "Chronic (89–Week) Feeding Study with Hydroxypropyl Distarch Phosphate, Starch Acetate, Lactose and Sodium Alginate in Mice" Fd. Chem. Toxic, 1986, pp. 825–834.

Joint FAO/WHO Expert Committee on Food Additives, "Evaluation of Food Additives: Some Enzymes, Modified Starches and Certain Other Substances", Jun. 1971.

Food and Drug Research Laboratories, Inc., "Subacute (90–Day) Feeding Studies With Treated With Adipic Acid and Acetic Anhydride", Oct. 1964, pp. 1–11.

Food and Drug Research Laboratories, Inc., "Subacute (90–Day) Feeding Studies With Treated With Acetic Anhydride", Sep. 1964, pp. 1–13.

(List continued on next page.)

Primary Examiner—Gary E. Hollinden
Assistant Examiner—Dameron Jones
Attorney, Agent, or Firm—Cushman Darby & Cushman IP Group of Pillsbury Madison & Sutro

[57] ABSTRACT

Delivery to the colon of fatty acids especially Short Chain Fatty Acids (SCFA) can be effected by covalently linking SCFA to a carrier that is preferably a form of carbohydrate, by an ester link. The SCFA is protected by its link with the carbohydrate through the small intestine, and where the carbohydrate is digestible in the small intestine such as a digestible starch, the starch can also be protected from digestion in the small intestine by the substitution. Levels of SCFA such as acetate, propionate and butyrate may be elevated to have beneficial effects in the prevention of colonic disorders such as rectal cancer, diverticulities, colitis, diarrhea and constipation.

118 Claims, 8 Drawing Sheets

OTHER PUBLICATIONS

Food and Drug Research Laboratories, Inc., "Subacute (90–Day) Feeding Studies With Treated With Epichlorohydrin and Acetic Anhydride", Oct. 1964, pp. 1–13.

Feron et al., "Sug–chronic toxicity test with a modified potato starch and an alginate in albino rates", Central Institute for Nutrition and Food Research, Jan. 1967.

Til et al., "Chronic (two–year) feeding study in rats with two chemically modified starches (starch acetate and hydroxypropl distarch glycerol) (Preliminary report)" Central Institute for Nutrition and Food Research, Feb. 1971.

Groot et al., "Observations in rat fed on diets containing five different chemically modified starches", Central Institute for Nutrition and Food Research, Jan. 1970.

Informatic Inc., "Monograph on Starches", Nov. 1974, pp. 24–46.

World Health Organization; Food Additives Series "Biological Data", 1982.

Joint F.A.O./W.H.O. Expert Committee on Food Additives; F.A.O. Nutrition Meetings Report Series 45A:7, 60–92, Bib No. 669.

Food and Agriculture Organization of the United Nations, World Health Organization, "Toxicological Evaluation of Some Food Colours, Emulsifiers, Stabilizers, Anti–Caking Agents and Certain Other Substances", Jun. 1969.

A. E. Stanley Manufacturing Company, Research Division, Decatur, Illinois, "Rat Test R–81" May 1, 1958, pp. 1–5.

FATTY ACID DELIVERY SYSTEM COMPRISING A HYDROLYZABLE BOND

This application claims benefit of international application PCT/GB94/00713, filed Nov. 17, 1994, published as WO95/13801 May 26, 1995.

FIELD OF THE INVENTION

This invention relates to an agent for use in food, dietary, and the like preparations, and to preparations, formulations and dietary compositions containing the agent. The invention is also concerned with a method of and pharmaceutical preparations for reducing the risk of certain colon disorders or for treating said disorders.

BACKGROUND OF THE INVENTION

Colonic health is associated with a number of factors, and a well known strategy in recent time to promote large bowel health has been by increased consumption of "fibre", a large proportion of which is not digested at all and acts, at least in part, by giving rise to greater bulk and moisture retention in the colon. This will be described below in more detail.

The fibre components of the human diet are generally gel-forming fibres such as pectins, gums and mucilages found in fruits, oats and barley; insoluble, structural fibres such as cellulose found in cereal brans; and storage polysaccharides such as guar and gums in legumes. There is some lignin as well, however, whilst it can be a significant part of animal diets, lignin contributes very little to the human diet.

A further polysaccharide, resistant starch, may well be regarded as fibre purely on functional grounds. Whilst starch is generally digestible in the small intestine of humans, absorption does not occur unless starch is completely depolymerized to glucose. A proportion of starch ingested by humans passes into the colon and nutritionists have termed this fraction resistant starch. The starch that passes into the colon has avoided the activity of the enzymes of the small intestine, the predominant class being the α amylases. Starches can acquire their resistant characteristic in a number of different ways, thus certain sources of starches are naturally resistant, such as those derived from raw potato and banana; those that are physically indigestible because they are present in partly milled grains and seed; or those that have retrograded after cooling following cooking. The range of starches have been classified by Englyst et al (1992) *Eur J Clin Nutr* 46 (Suppl. 2): S33–50). Whilst non starch polysaccharides (NSP) and lignin are intrinsically indigestible, resistant starch can be digested in the colon, and fermentation of resistant starch plays an important role in colonic health, which role will also be described in more detail below.

There are two major subdivisions of NSP: water soluble and water insoluble. Cellulose is the most common insoluble NSP, while pectin and guar gum are two common soluble NSP.

Preparations such as wheat bran, high in insoluble NSP, accelerate transit in the stomach and small intestine and in the colon. This effect apparently arises due to physical bulking, as wheat bran increases stool mass in an apparently dose dependent manner following the passage of largely unmodified bran. Similar increases in bulk have been noted with other insoluble NSP such as cellulose.

Soluble NSP have radically different effects on transit and in the small intestine, slow the passage of digesta. Guar gum in biscuits and drinks slows gastric emptying and the passage of ingesta in the small intestine. This effect is due to the viscosity of the soluble NSP. In the colon effects of NSP seem to be due to the extent to which they are fermented by the microflora.

On passage from the ileum, NSP are metabolised by the anaerobic microflora of the caecum and colon which produce the enzymes necessary for polysaccharide hydrolysis and catabolism. Fibre breakdown is effected by bacterial species very similar to those found in the rumen of obligate herbivores and with very similar products: gases (carbon dioxide, methane and hydrogen) and short chain fatty acids (SCFA). The principle SCFA formed from NSP fermentation are the same as in the rumen, i.e. acetate, propionate and butyrate, and in the rough molar proportions 60:20:20. These three acids contribute some 80–90% of total colonic SCFA, the remainder being branched chain and other fatty acids formed from the breakdown of dietary and endogenous protein. SCFA are natural by-products of normal colonic bacterial metabolism. In addition to the direct production of SCFA from carbohydrate fermentation, it appears that in individual humans (and possibly some animal species) there is an acetogenic fermentation in which acetate is formed by bacterial condensation of some of the gases released from NSP breakdown.

SCFA concentration measurements that have been determined in humans indicate that SCFA concentrations are higher in the proximal colon than in the distal colon.

NSP are major fuels for colonic fermentation, and the faecal recovery of many soluble NSP is poor. Numerous animal studies have shown higher colonic SCFA in animals fed soluble NSP, and some show increased bacterial mass. In the colon it is most probably that many of the effects of soluble NSP and resistant starch are mediated through SCFA. However products high in insoluble NSP also can raise colonic SCFA in animals and increase faecal SCFA excretion in humans. It is probably incorrect to assume that products such as wheat bran and rice bran are totally inert. Their effects may be mediated through both physical bulking and SCFA.

If there is one single aspect of fibre physiology which is almost beyond question it is its role in the prevention and management of simple constipation. Fibres vary enormously in their effects on bowel function. Cereal brans such as wheat and rice brans that are high in insoluble NSP appear to be most effective in easing problems of laxation through shortening transit time, softening stools through raised water holding, increasing stool volume and weight in the form of bacteria and undigested and nonfermentable material. While wheat bran increases faecal bulk in an apparently dose dependent manner, fibre high in soluble NSP have unpredictable effects—presumably due to colonic fermentation.

Until 1970 diverticular disease was treated with low residue diets on the assumption that coarse fibre particles might lodge in the colon, aggravating the inflammation and mucosal herniation. However, studies have consistently demonstrated that therapeutic effects of wheat bran in the diet. There is evidence also that unless fibre is included in the diet, symptoms may recur after surgery indicating that fibre is both preventative and therapeutic. Any role for soluble NSP and resistant starch in diverticular disease is uncertain.

Although it is convenient to explain the actions of fibre-rich foods such as wheat bran solely in terms of stool mass, this is not quite correct. Feeding of foods containing non-starch polysaccharides leads to increased faecal bulk in humans and animals. Products such as wheat bran increase stool mass in humans in a dose dependant manner. However, the increase in faecal bulk in humans eating mixed diets is considerably higher than predicted from their non starch polysaccharide content—the "carbohydrate gap" (Stephen (1991) Can J Physiol. Pharmacol 69: 116–20). Starch is thought to fill this gap and contribute to the greater faecal bulk through bacterial proliferation, by providing a fermentation substrate, (both glucose, and certain SCFA) as well as providing physical bulk. Cummings & McFarlane calculated that in the British diet, about 8–40 g of enzyme resistant starch cold enter the colon daily, compared with 8–18 g of nonstarch polysaccharides (Cummings and Macfarlane (1991) J Appl Bacteriol 70: 443–459).

Measures that prevent diarrhoea have been analysed and it would seem to be most effective with fibre mixtures rather than supplements containing a single NSP. However there are other subtle effects that appear also to play a role.

The pH range of digesta in the human colon needs to be established but in pigs on high fibre diets it ranges from approximately 6 in the proximal colon to >7 in the distal colon. The pKa of short chain fatty acids is <4.8 so that in the colon they are present largely as anions. SCFA are absorbed in the non-ionic form and are then ionized at intracellular pH to $H^+$ and SCFA which are then exchanged for luminal $NA^+$ and $Cl^-$ respectively. Some of the SCFA are also metabolized to $HCO_3$ which is also exchanged for chloride ions. Therefore SCFA is beneficial in facilitating transporting ions that play an important role in metabolism.

Thus SCFA do not contribute to osmotic load to any great extent and may ameliorate diarrhoea through removal of sodium and water from the colonic lumen. However, because SCFA are present largely as anions, their absorption is relatively slow. For this reason and their presence in faeces, SCFA have been assumed to cause diarrhoea. That view is no longer held and diarrhoea is thought to occur only when the osmotic pressure of simple and complex carbohydrates in the colon raises the fluid volume excessively and bacteria cannot break down the carbohydrate sufficiently rapidly. In fact SCFA may have longer term preventative effects by stimulating growth of colonocytes thereby increasing the capacity of the colon.

Epidemiological data have shown that the level of dietary fibre is inversely related to incidence of bowel cancer and a meta-analysis of a large number of studies showed that fibre was protective in over 50%. It is not possible to discriminate the type of NSP or foods that were effective. Indeed, the factor most strongly associated with this disease is the intake of meat or fat. Since animal protein intake and consumption of cereal and plant foods are inversely related, the association between fibre and cancer is often weakened in a multivariate analysis. Confusion exists also because of conflicts between data from animal and in vitro experimentation and those emerging from human studies. A very recent study by Cassidy et al (British Journal of Cancer 69; 937–942 (1994)) has shown that starch plays a protective role.

The role of fibre in the maintenance of colonic mucosal integrity is understood imperfectly. Experiments with animal models such as pigs have shown that the weight and thickness of the colon is increased with diets high in fibre—consistent with greater cell growth. The effect is not confined to fibre as Goodlad and Mathers ((1990) Brit J Nutr. 64; 569–587) have obtained similar increases in the hindgut of rats fed diets high in resistant starch. Other studies with rats have shown that the increase is probably not due to increased mass of digesta since an inert faecal bulking agent (kaolin) did not stimulate mucosal proliferation. In the same experiments it was shown that colonic infusion of short chain fatty acids enhanced colonocyte proliferation suggesting that they were the trophic agents (Sakata J Nutr Sci Vitaminol 1986; 32: 355–362). It is likely that only propionate and butyrate are involved in these effects. Propionate is known to enhance colonic motility possibly through stimulating blood flow (Kvietis and Granger, Gastroenterol (1981); 80: 962–969). Butyrate is thought to play a most critical role in the cell biology of colonocytes and is preferred over acetate and propionate as their oxidative fuel (Cummings, Gut (1981) 22: 763–779). Butyrate inhibits the proliferation of malignant cells from the human colon in vitro via inhibition of DNA synthesis an arresting of the cells in the $G_1$ phase. Induction of cell differentiation has also been demonstrated, an observation that is consistent with the fact that when cells differentiate they lose their capacity to proliferate. Butyrate also enhances the capacity of colonic cells to repair DNA damage (Smith, Carcinogenesis (1986) 7: 423–429). All of these effects require physical presence of the acid and are obtained at butyrate concentrations similar to those found in the colon in vivo. A particular point of interest is that there is evidence that human faecal inocula ferment starch to butyrate (Pilch (ed) Physiological effects and health consequences of dietary fibre. Bethesda Md. USA: FASEB 1987) and such production might explain inconsistencies in epidemiological data where fibre is not always protective but plant foods are beneficial.

Several studies in animal models have shown that supplementation of the diet with fibre protects against tumours induced with chemical carcinogens such as dimethylhydrazine (DMH), azoxymethane (AOM), and 3,2-dimethyl-4-aminobiphenyl (DMAB). Meta-analysis of these studies by the Federation of American Societies for Experimental Biology (FASEB) (Pilch (1987) supra) showed that wheat bran was more effective than pectin or cellulose in reducing lesion formation induced by chemical carcinogens. These data are paradoxical if one considers that soluble NSP might be expected to be fermented to SCFA more than wheat bran. However, rat studies show that wheat bran gives relatively higher concentrations of butyrate in hind-gut digesta than soluble NSP. In addition, wheat bran seems to bind chemical carcinogens and to reduce their colonic concentration and might be doing so in the animal model systems. A protective action of wheat against experimental carcinogenesis cannot be dismissed.

It is believed that butyrate enhances the proliferation of normal cells but may exert antineoplastic effects on susceptible cells and significantly retards the growth of human colon cancer cells in vitro (Kim et al In Malt and Williams (Eds) Colonic carcinogenesis. Lancaster MTP Press, (192); Falk Symposium 31: 317–323). A recent study which has shown that the molar proportion of butyrate is significantly lower in faeces from patients with adenomatous polyps (Weaner et al Gut (1988); 29: 1539–1543) is of special interest as it suggests that short chain fatty acid production is abnormal. In a feeding trial in patient with polyposis, a wheat bran supplement appeared to reduce polyp numbers and size (De Cosse et al J Nat Cancer Inst (1989); 81: 1290–1297). This is also a very promising study and indicates that insoluble NSP may be protective. Of particular interest is the fact in this study an insoluble NSP (which also enhances lactation) was protective. The situation was soluble NSP and resistant starch is unknown.

It is suggested that lack of luminal SCFAs lead in the short term to muscular atrophy and in the long term to 'nutritional colitis'. This is especially evident in diversion colitis, which develops after complete diversion of the faecal stream and subsides after restoration of colorectal continuity. Irrigation with SCFA for 2–3 weeks has resulted in resolution of inflammation. Ulcerative colitis has also been successfully treated using butyrate enemas. (Scheppach et al (1992) *Gasteroenterology;* 103: 51–56.) Generally anti-inflammatory measures, such as the use of anti-inflammatory drugs, do have side effects and in particular where large doses are used to overcome the natural degradation of those drugs in the small intestine before they reach the colon. The use of SCFA on the other hand is seen as particularly beneficial because they are naturally occurring and replace the use of anti-inflammatory drugs such as NSAIDS (nonsteroidal anti-inflammatory drugs), corticosteroids and other anti-inflammatory drugs.

Thus there is growing evidence that products resulting from bacterial fermentation of carbohydrates in the colon lead to some specific advantages. It appears that specific advantages are derived from elevated level of Short Chain Fatty Acids (SCFA) such as acetic, propionic and butyric acids. The precise effector of such benefits, in most if not all instances, has not been conclusively shown, however it is apparent that one or more of the SCFA do have beneficial effects.

Accordingly it is advantageous to provide a means of elevating the level of SCFA in the colon so that the advantages can readily be provided. Other fatty acids may also have a beneficial effect.

One difficulty with such treatments however is that if the SCFA's or other Fatty Acids are simply administered unprotected orally that they are very rapidly absorbed or degraded and substantially no SCFA survives to arrive at the colon. SCFA's have been administered rectally especially in the treatment of forms of colitis as described above. Rectal administrations however are generally not considered desirable, requiring the attendance of at least nursing staff and being generally unpleasant for the recipient, especially should regularly repeated doses be required.

It is therefore desirable that an alternative route be adopted, such as for example an oral route. To arrive at an appropriate means of administering such product requires that the medium be protected by the physical and chemical and enzymatic attack of the alimentary tract to arrive at sufficiently high levels in the colon before being becoming available.

One property that is desired however is that the application throughout the colon does not lead to localized high concentrations that might damage colonocytes, and have either adverse effects. Accordingly providing SCFA is a capsule protected from cleavage in the remainder of the alimentary tract is seen as not optimal. Slow release SCFA's present in a gel made of a modified starch which gives a slow release is an alternative possibility however a difficulty associated with such an approach is that the level and duration of the release is difficult to control.

Furthermore it is desired that reasonable control is achieved to deliver SCFA to the distal colon in effective quantities, because many of the disorders associated with the bowel are more associated with the distal colon. It is also desirable to minimise the loss of SCFA to the remainder of the alimentary tract.

It is an object of this invention to provide a delivery mechanism that allows for delivery of Fatty Acid to the colon, and more preferably to the distal colon.

It is an object of another form of the invention to provide a method for improving bowel health by delivery of Fatty Acid to the large bowel.

It is an object of a further form of the invention to provide a method of prevention of certain disorders of the colon.

It is an object of a yet further form of the invention to provide a method of treatment of certain disorders of the colon.

It is an object of a still further form of the invention to provide an agent for the treatment or prevention of certain bowel disorders.

SUMMARY OF THE INVENTION

It has been found according to this invention that by ingestion of an agent comprising a SCFA (Short Chain Fatty Acid) covalently linked to a carrier that delivery of the SCFA can be effected to the colon.

It is known to use an acetylated starch in the production of plastics and in the foods industry however it use is as a means of clarifying food products and as a thickener for foods. It is permitted under the Australian NFA food regulations to use a acylated starch by substitution with 2.5% w/w of acetic anhydride. In the event of a 100% efficient reaction this would result in a degree of substitution of 0.04 That is to say that less than 1 in 25 glucose molecules. It is thought that such a degree of substitution will not give sufficient boost to the acetate level in the colon. It has not been heretobefore known to use this material to deliver SCFA to the colon or known for its nutritive value.

The SCFA that are considered to be most beneficial in treatment or prevention of certain colonic disorders are those fatty acids with carbon chain lengths of 2, 3 and 4, namely Acetate, Propionate, and Butyrate. However other SCFA may also have beneficial effects and therefore the term SCFA includes branched chain or substituted short chain fatty acids. There is doubt whether formate (C1) is of benefit, in fact elevated levels ae considered to have been implicated with adverse effects. SCFA of other lengths may also be may also be beneficial so that the term SCFA is to be understood to include those Fatty Acids with a chain length in the range of between and including 1 to 6 carbons. It is also to be understood that Fatty acids with longer carbon chain lengths may also be beneficial and may be covalently bonded to a carrier in a similar fashion. The fatty acids envisioned by this invention are all susceptible to breakdown before arriving at the colon, unless protected.

The carrier to which the SCFA is bonded is preferably a carbohydrate, although other carriers may also be used. Using a carbohydrate has several advantages, largely because of the availability of carbohydrates in commercial quantities and because the effects of carbohydrates in the alimentary tract are relatively well understood. Some forms of carrier are undesirable. For example protein is undesirable because after fermentation of the protein by products are formed that have an adverse effect on the colon.

Several forms of carbohydrate may be used as a carrier, and these may include but are not limited to pectins, gums and mucilages, cellulose, hemicelluloses, gums, inulin, and oligosaccharides.

Any suitable source of pectin may be used and the following are illustrative of the types that might be used:- High, medium and low methoxylated pectins, high, medium and low gel strength pectins. The pectin may be derived from any number of sources which sources may include from apples, oranges and lemons.

Any suitable source of gums may be used and the following are illustrative of the types that might be used:- guar, xantham, arabic, tragacanth, locust bean and psyllium. Modified and artificial gums may also act as a carrier.

Any suitable source of cellulose may be used and the following are illustrative of the types that might be used:- Microcrystalline, Methyl celluloses, hydroxypropylmethyl cellulose and carboxymethylcellulose.

Of the oligosaccharides the following could act as a carrier, fructo-oligosaccharides, galacto-oligosaccharides, maltodextrins, and modifications and derivatives thereof.

The use of simple sugars such as glucose, fructose, galactose, sucrose and lactose, is limited because these may result in osmotic effects that lead to osmotic diarrhoea if administered at levels that are too high.

One of the preferred forms of carrier is a starch because it can be fermented by microorganisms in the colon, and accordingly provides for extra nutrients for bacterial bulking in the colon, as well as separately providing a further source of SCFA additional to the SCFA linked to the carrier.

The starch may be a starch that is digestible in the small intestine. Such digestible starch is protected to some extent from the degrading effects of α amylases in the small intestine by the SCFA The extent that the starch is protected however will depend upon the degree of substitution, and if there is only a relatively low degree of substitution, then the starch will rapidly be degraded and there will be relatively good access by the low levels of esterases that exist in the upper alimentary tract to the ester bonds to cleave many of the SCFA's from the carrier thereby leading to ineffective delivery to the colon. It may therefore be advantageous to use a resistant starch that is already resistant to digestion in the small intestine, but that is digestible in the colon. This will maximize the delivery of starch, and probably SCFA.

The term starch is understood to include all forms of starch including modified starches, and either by physically, enzymically, esterification, oxidation acid cleavage, and reaction with difunctional reagents, and includes those forms of starch that might be included in the classification RS2 and RS3. Starch can be derived from a great many sources, and may be derived, for example, be native starches from wheat, potato, tapioca, maize, rise and oats. The carrier may be a resistant starch—resistant to digestion because of physical size, starch type (e.g. high amylose maize), potato, green banana and legumes such as peas or due to retrogradation induced by granular disruption, hydration and reassociation in an enzymatic resistant form.

It is to be understood that the carbohydrates listed may be modified, either singly or multiply though the use of:

heat and/or moisture physically (e.g. ball milling)

enzymatically (e.g. α or β amylase, pullulanase or the like)

chemical hydrolysis (wet or dry using liquid or gaseous reagents)

esterification (eg chemical with propylene oxide)

oxidation cross bonding with difunctional reagents (e.g. sodium trimetaphosphate, phosphorous oxychloride)

carboxymethylation or other forms of modification known to those practices in the art. These can occur in aqueous and nonaqueous environments. This list of modifications is not intended to be exhaustive or limiting.

Where it is desired to deliver only one SCFA then a non-digestible carrier, i.e. one that is not degraded by bacterial enzymes of the colon is preferably used, leading to more accurate control over delivery of a single SCFA, and this may have beneficial effects on the treatment or prevention of certain disorders. The degree of substitution coupled with the quantity of the agent ingested can be used to regulate the level of one or more SCFA delivered to the colon.

For pharmaceutical preparations it is generally convenient to have a water soluble preparation, and therefore where treatment of a disorder of the colon is intended, it is preferable that the carrier is water soluble. The pharmaceutical may perhaps take the form of a powder, a measured quantity of which can be solubilized in water, and ingested. The term soluble is understood not to be taken in its strictest sense, but also to include what would appear to be soluble to a user, and therefore may include the ability to form a gel. The function is simply to provide a means of easy delivery of the agent.

Another form of administering the agent could be in a dry form so that for example a food or perhaps the agent within a solid ingestible carrier.

Examples of food preparations that might include the agent are baked products such as bread, biscuit, or cakes, dairy and dairy substitute food and/or confectionary products such as milk products including icecream, yoghurt and milk based drinks, cereal food preparations and edible oil compositions such as salad dressings. The agents of the invention may be included as a thickening agent in food preparations and may be used to replace normal thickening agents such as starch.

The invention is beneficial in the maintenance of colonic health, and includes the method of reducing the risk of any one or more of the colonic disorders selected from the following; colonic cancer, constipation, diverticulitis, colitis and irritable bowel, and includes the steps of orally taking an effective dose of the agent according to this invention at regular intervals.

The daily dosage rate for a SCFA substituted onto a resistant starch such as a resistant maize starch at a degree of substitution of 0.1 may be in the range of about 5 to 20 grams per day although other dosage rates may be employed. It would be expected that similar dosages rates would be appropriate for other forms of the agent.

It is to be understood that this invention also has application to both animals as well as humans and accordingly the SCFA substituted carrier can be used either in the treatment of animal colonic disorders or in the prevention of colonic disorders and may therefore be included in various forms of pet food.

The bond between the SCFA and the carrier (carbohydrate) is preferably one that can be cleaved by an agent in the bowel to give free SCFA which can then be absorbed. It is to be understood that the cleavage can be either by a single enzyme, or may take a second step where that enzyme is present in or around the colon.

The bond between the SCFA and the carrier is preferably an ester bond, because the capacity of the microbial flora of the large bowel to hydrolyse ester bonds is far greater than is the capacity of other portions of the alimentary tract to do so. Furthermore because hydroxyl groups are generally abundant amongst many carbohydrates there is a potential for a large range of densities of substitution and the ability to substitute is relatively easy.

Other forms of bonding may include amide bond to amino sugars, however such sugars are relatively rare in unmodified carbohydrates, and the rarity limits the extent of substitutions that might be made, or alternatively limits the usefulness to modified carbohydrates, some of which might have other specific advantages. Alternatively the link may be different where substituted SCFA's are used.

The degree of substitution can depend upon the desired outcome, and degree of bulk or bacterial build-up that is desired. For example where a SCFA is bonded to a carbohydrate it is considered unlikely that the esterases will be able to access the ester bond between the sugar moiety and the SCFA moiety if more than one SCFA's are present per sugar molecule. Furthermore it is likely that the surface characteristics of the carbohydrate will be modified to an extent that the carbohydrate will no longer be water soluble. Accordingly it is preferred that the degree of substitution be less than one per sugar moiety.

The term degree of substitution, as will be understood, is not to imply that each carrier molecule is evenly or equally substituted, but is to be taken as meaning an average degree of substitution. As in most substitution reactions, product molecules with a range of substitutions will result.

Where a digestible starch is used it is considered unlikely that any significant protection to cleavage will result if less than one SCFA is bonded for every twenty sugar molecules, accordingly in a preferred form of the first aspect of the invention the degree of substitution is selected from within the range of 0.05 to 1 SCFA per sugar moiety. Generally however for ease of synthesis and handling a range of between about 0.1 and 0.5 is convenient. Other carbohydrates however are able still to be handled and solublized where the degree of substitution is greater than one and therefore the generally the degree of substitution of selected from the range of 0.05 to 2.

EXAMPLES

Figure 1:
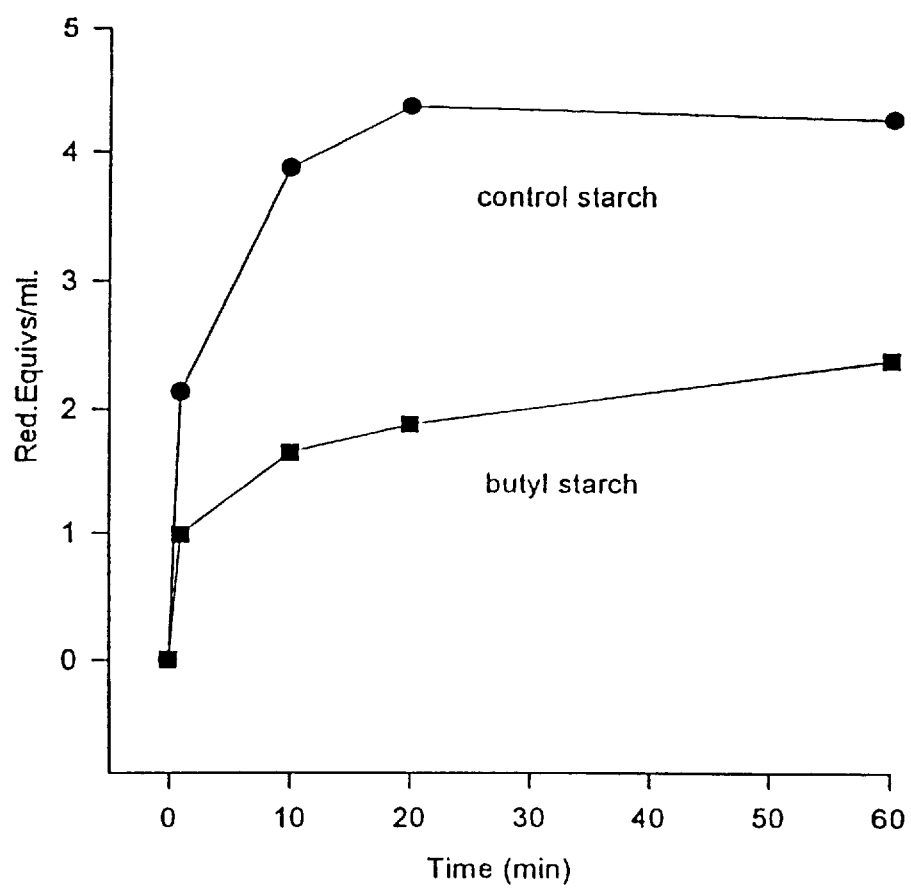
FIG. 1. Release of reducing equivalents from starch and bytyrylated starch by amyloglucosidase, FIG. 2. The concentrations ($\mu$mol/L) and total pool sizes of SCFA found in caeca and distal colons fed butyrylated starches, FIG. 2a. Caecal SCFA concentration FIG. 2b. Caecal SCFA pools FIG. 2c. Distal colon SCFA concentration FIG. 2d. Distal colon SCFA pools FIG. 3. Release of reducing equivalents by $\alpha$ amylase from acylated starch products. The values for the control starch are shown in FIG. 3c, FIG. 3a. Starch acetate FIG. 3b. Starch butyrate FIG. 3c. Starch propionate FIG. 4. Activity of $\alpha$-amylase with starch butyrates as substrates, FIG. 5. Levels of SCFA in the caecum of rats fed acyl starch products, FIG. 6. Pools of SCFA in the caecum of rats fed acylated starch products, FIG. 7. Levels of SCFA in the distal colon of rats fed acylated starch products, FIG. 8. Pools of SCFA in the distal colon of rats fed acylated starch products, FIG. 9. Total starch (mg) present in the caecal and distal colon samples of rats fed acylated starch products.
Figure 2A:
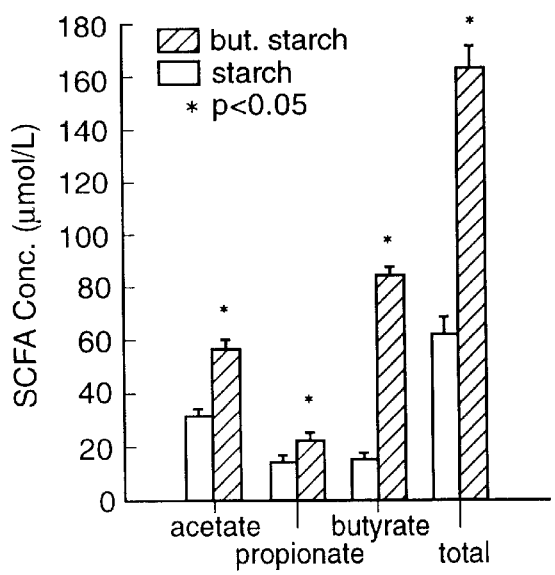
Figure 2B:
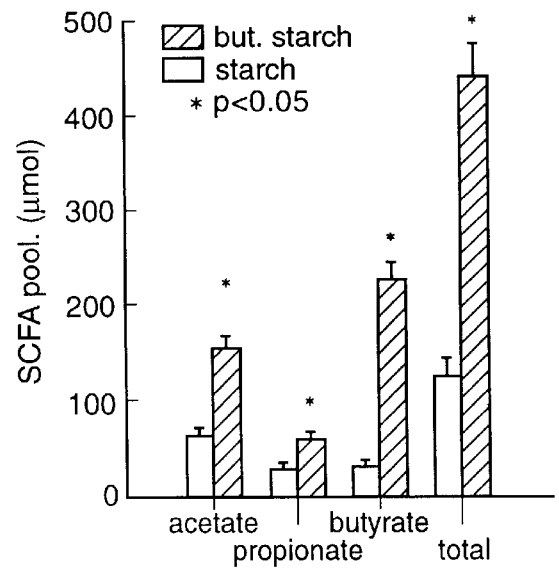
Figure 2C:
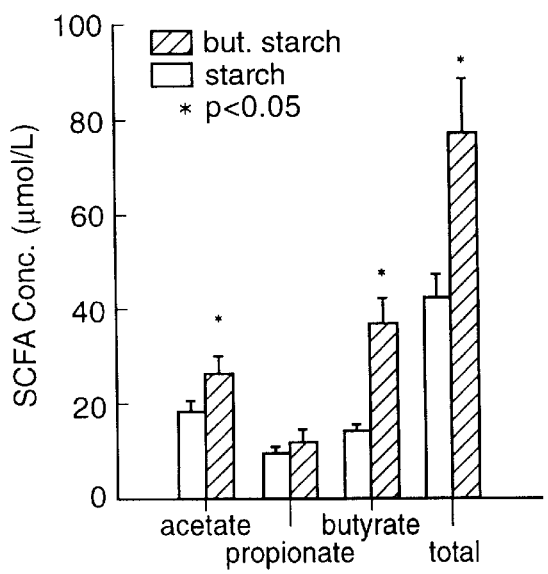
Figure 2D:
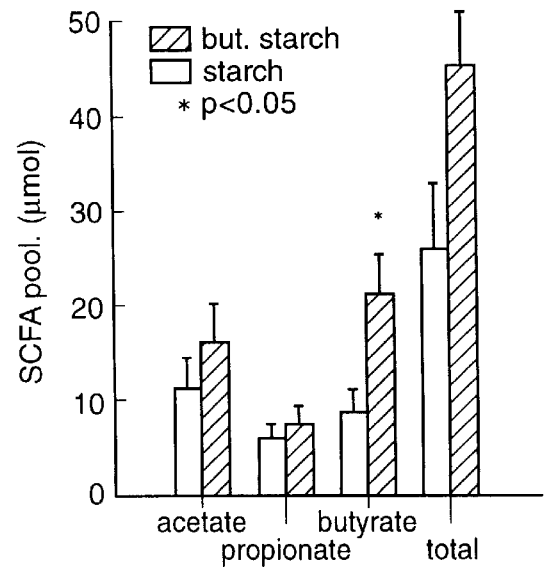

For a better understanding the invention will now be described with reference to the examples.

Maize starch was chosen as the trial carrier, and was esterified at three levels with the anhyrides of acetic, butyric and propionic acids. A control starch was also produced by sham treatment of maize starch. Untreated maize starch is digestible by the small intestine.

Example 1.
PREPARATION OF A BUTYRYLATED STARCH

There are several ways in which the acylation of starches can be brought about. The method employed initially involves the use of an aprotic solvent (dimethyl sulphoxide, DMSO), a base catalyst (1-methylimadazole, 1-MID) and butyric anhydride. It was thought that this approach would be successful because the DMSO would dissolve and hence randomise all the starch molecules. The uniformly dispersed starch molecules could then be partially but evenly butyrylated.

Preliminary trial

Initially a small scale experiment was conducted to determine the effect of reactant ratios on the degree of substitution (DS).

Method

1) In 5 tubes, maize starch (0.5g) was dissolved in DMSO (30 mL) by stirring overnight at room temperature.
2) 1-MID and butyric anhydride was added to the tubes as shown in the Table 1

TABLE 1

Reagent amounts and DS of butyrylated starches prepared in a small preliminary trial.

| Sample No. | 1-MID (mL) | Butyric Anhydride (g) | DS |
| --- | --- | --- | --- |
| 1 | 0.1 | 0.00 | 0 |
| 2 | 0.1 | 0.25 | 0.25 |
| 3 | 0.1 | 1.00 | 0.5 |
| 4 | 0.1 | 1.5 | [1]ND |

[1]ND- not determined

3) The mixtures were stirred for 1 h. Water (30 mL) was added to decompose any remaining butyric anhydride. Ethanol (4 vols) was then added to precipitate the starch. The precipitate was washed twice with ethanol (80%) and once with acetone, then dried and milled through a 0.5mm screen.
4) Sample 4 did not hydrate when added to water and thus was likely to have a high DS and not be soluble in water and therefore and be biologically inactive.
5) Aliquots (10 mg) from samples 1, 2 and 3 were saponified in 50 mL of 0.1 M NaOH and the volume was then adjusted to 100 mL. The concentration of butyric acid in the mixture was determined by GLC analysis.

Results

The DS of samples 1, 2 and 3 are recorded in Table 1. Sample 4 was not determined.

Conclusions

The results demonstrated that altering the amount of butyric anhydride affected the DS. The ratio of reactants used in sample 2 were used in a large scale procedure.

Large Scale preparation

Method

1) Maize starch (110 g) was dissolved in DMSO (6 liters) in a 30 L stainless steel drum sitting on a stirrer overnight.
2) 1-Methylimidazole (1-MID, 20 g, base catalyst) and 50 g of butyric anhydride were added.

4) The mixture was allowed to stand for 4 h at room temperature with occasional stirring by hand. (The viscous nature of the mixture precluded mechanical stirring with the stirring plate and bar stirrer.
5) Water (6 L) was added to decompose any remaining butyric anhydride.
6) Drum ethanol (24 L) was added to precipitate the starch.
7) The butyrylated starch was recovered and washed repeatedly in 80% ethanol (4×1 liter) to remove DMSO and butanoic acid.
8) The starch (105 g) was dried, (40° C.) milled into a powder, weighed and, analysed.
9) A further 110 g of starch was dissolved in DMSO and precipitated with ethanol in a sham preparation procedure to provide a control starch.
10) The DS was determined using GLC analysis.

Results

The large scale procedure successfully produced a starch with one butyryl group for each 3–4 glucose units is approx. DS=0.25 (GLC analysis).

Example 2.
EFFECT OF BUTYRYLATION ON THE IN VITRO DIGESTION OF STARCH BY AMYLOGLUCOSIDASE Amyloglucosidase hydrolyses the $\alpha$ (1-4) and a(1-6) bonds of starch randomly. It is considerably more efficient than $\alpha$-amylases. For this reason it was chosen for initial trials to determine whether acylation of starch would inhibit the activity of starch degrading enzymes.

Method

The butyrylated starch and a control starch (dispersed in DMSO and recovered by ethanol precipitation) were dissolved in acetate buffer (20 ml, pH5) by heating at 100° C. for 2 hours and then by stirring at room temperature overnight. The total amount of anhydroglucose units of each was the same (5 mg/mL). An aliquot (5 mL) of each was taken and amyloglucosidase (0.2 mL) was added and the mixtures were incubated at 55° C. The release of reducing equivalents was followed colorimetrically (2,5 dinitrosalicylic acid reagent, DNS) by periodically removing aliquot (0.2 mL). Calibration was against a set of glucose standards.

Results

1) A linear calibration curve was obtained for the DNS reagent determination of reducing.

TABLE 2

Release of reducing equivalents by amyloglucosidase from a control starch and from a butyrylated starch.

| Time (min) | Control Starch (Red. Equ.) | Butyrylated Starch (Red Equ.) |
| --- | --- | --- |
| 0 | 0 | 0 |
| 1 | 2.13 | 0.98 |
| 10 | 3.87 | 1.64 |
| 20 | 4.36 | 1.87 |
| 30 | 4.26 | 2.37 |

2) The release of reducing equivalents by amyloglucosidase was faster in the control starch than in the butyrylated starch as shown in the Table 2 and FIG. 1.

Conclusions

Butyrylation of starch reduced the rate of hydrolysis considerably compared to the control starch. The data suggest that butyrylation will protect the starch from digestion in the small intestine to some extent and may result in butyrylated starch entering the large intestine.

Example 3.
EFFECT OF FEEDING BUTYRYLATED STARCH ON HINDGUT SCFA LEVELS IN THE RAT Two groups of rats were fed purified diets (based on AIN (American Institute of Nutrition) recommendations, Table 3) containing butyrylated starch (n=6) and a control starch which had gone through a sham treatment which acted as a control (n=5). The rats were killed after 3 days and their hindgut contents removed. The levels of SCFA in the caecum and distal colon were determined. The results are shown in Table 4 and FIG. 2.

TABLE 3

Composition of trial diets.

| Ingredient | Composition (g/kg) |
| --- | --- |
| casein | 200.0 |
| methionine | 1.5 |
| sucrose | 50.0 |
| starch (corn) | 401.5 |
| cellulose | 50.0 |
| choline tartrate | 2.0 |
| corn oil | 100.0 |
| mineral mix | 35.0 |
| vitamin mix | 10.0 |
| starch (butyl or control starch*) | 150.0 |

*starch receiving a sham treatment.

Results

The data in Table 4 and FIG. 2 demonstrate that feeding the butyrylated starch significantly increased both the concentration and pool sizes of SCFA and the relative levels of the SCFA in both the caecum and distal colon. The levels of butyrate were greatly increased both in the caecum and the distal colon.

TABLE 4

Concentrations ($\mu$mol/L) of acetate, propionate and butyrate in the caeca and distal colons of rats fed the control starch and butyrylated starch

|  | Control Starch | | | But. Starch | | |
| --- | --- | --- | --- | --- | --- | --- |
|  | ace. | pro. | but. | ace. | pro. | but. |
| Caecum | | | | | | |
| 1 | 24.2 | 8.0 | 6.0 | 49.2 | 14.6 | 68.1 |
| 2 | 29.9 | 10.9 | 13.2 | 65.5 | 24.8 | 93.1 |
| 3 | 33.3 | 18.9 | 18.3 | 66.3 | 30.1 | 85.5 |
| 4 | 30.0 | 14.6 | 19.3 | 56.9 | 22.3 | 83.7 |
| 5 | 40.3 | 18.0 | 17.7 | 50.7 | 27.3 | 89.4 |
| 6 | | | | 51.1 | 14.7 | 80.3 |
| mean | 31.5 | 14.1 | 14.9 | 56.6 | 22.3 | 83.5 |
| Dist. Colon | | | | | | |
| 1 | 25.3 | 10.2 | 10.3 | 27.1 | 10.3 | 35.5 |
| 2 | 12.4 | 5.6 | 9.7 | 19.1 | 8.2 | 27.3 |
| 3 | 24.2 | 14.0 | 19.1 | 30.4 | 14.7 | 34.6 |
| 4 | 13.1 | 8.2 | 16.7 | 38.8 | 21.4 | 58.6 |
| 5 | 19.5 | 11.3 | 15.9 | | | |
| 6 | | | | 21.2 | 8.2 | 30.5 |
| mean | 18.8 | 9.9 | 14.3 | 27.3 | 12.6 | 37.3 |

Conclusions

The experiment demonstrated that butyrylated starch could be used to modify the levels of SCFA in the hindgut of rats. This is achieved by firstly inhibiting the digestion of the starch in the small intestine thus providing more fermentable substrate which in turn results in an increase in all the SCFA levels in the hindgut. The second effect is through the release of butyrate as can be seen by the very much higher levels of butyrate achieved by administration of the butyrylated starch.

Example 4.
INFLUENCE OF ANHYDRIDE CONCENTRATION ON THE DEGREE OF SUBSTITUTION OF STARCHES.

In order to see whether degree of substitution of starches could be easily controlled by influencing the level of anhydride in the reaction mixture the following experiment was performed.

Method
1) Maize starch (36.6 g) was dissolved in DMSO (2 L).
2) Portions (200 mL) were then dispensed into conical flasks (250 mL).
3) 1-MID was added and anhydride according Table 6.
4) The amount of organic acid released upon saponification was determined by a titrimetric method (detailed elsewhere). The effect of the different levels of anhydride are also shown in Table 6.

TABLE 5

The effect of anhydride level on degree of substitution in the preparation of Acylated Starch products.

|  | acetylation | | | propionylation | | | butyrylation | | |
| --- | --- | --- | --- | --- | --- | --- | --- | --- | --- |
| 1-MD[1] (mL) | 0.6 | 0.6 | 0.6 | 0.6 | 0.6 | 0.6 | 0.6 | 0.6 | 0.6 |
| anhydr[2]. (g) | 0.5 | 1.07 | 2.1 | 0.7 | 1.41 | 2.82 | 0.8 | 1.66 | 3.3 |
| DS[3] | 0.20 | 0.38 | — | 0.19 | 0.34 | — | 0.16 | 0.29 | — |
| % wt[4] | 5.06 | 9.10 | — | 6.34 | 10.70 | — | 6.61 | 11.19 | — |

[1]1-methylimidazole - base catalyst.
[2]acetic, propionic or butyric anhydride.
[3]degree of substitution
[4]level of acyl group as a percentage of the weight.

Results

The data in Table 5 indicate that the DS of the modified starches can be manipulated by adjusting the amount of anhydride used in the reaction mixture. The samples in which the highest level of anhydride were used were not analysed as this material failed to be recovered by ethanol precipitation. This indicated that the material was highly substituted and hence soluble in more organic solvents.

Example 5.
LARGE SCALE PRODUCTION OF ACETYLATE, PROPIONYLATED AND BUTYRYLATED STARCH.

The large scale preparation of acetylated, propionylated and butyrylated starch was accomplished as follows.
1) DMSO (24 L) was heated to above 80° C. with an immersion heater in a metal vessel under constant stirring.
2) The heater was removed and maize starch (440 g) was added slowly to the stirring DMSO through a domestic sieve to ensure uniform dispersement (to avoid clumping). The mixture was stirred constantly for 1 h by which time all the starch had dissolved to leave a clear, viscous solution.
3) 1-MID (80 mL) was added and anhydride (acetic - 85 mL, propionic - 132 mL, butyric 170 mL). These volumes were estimated from the previous experiment to give DS=0.25
4) After 4 h incubation the excess anhydride was decomposed by addition of 3 L of water and the reaction mixture was poured into 2 vols of ethanol.
5) The precipitated Acylated Starch product was washed with ethanol (80% v/v) several times to remove the DMSO and other reactants and dried at 40° C. in a hot air room.
6) A control starch went through a sham procedure in which no 1-MID or anhydride was added to the starch.
7) The starches were ground to a fine powder and analysed.

As the recovery of starches (a little under 400 g) was not quite enough to provide material for a rat feeding trial further batches of starches were prepared.
1) 600 g of maize starch was dissolved in hot DMSO (30 L)
2) The mixture was partitioned into 3 equal portions
3) 36 mL of 1-MID was added to each followed by the anhydrides (acetic, 38.63 mL, propionic, 60 mL and butyric 77 mL)
4) The mixtures were stirred frequently for 4 h and the Acylated Starch products starches were recovered as described above and analysed.

The Acylated Starch products from each preparation were combined following analysis and reanalysed.

Results

The DS of each of the Acylated Starch products produced in the two procedures described above were similar. Combining the two batches of each the products produced enough material to use in subsequent feeding trials.

TABLE 6

Acylation (DS) achieved in acylated starch products by the large scale procedure and level in combined products.

|  | Acetylated Starch | Butyrylated Starch | Propionylated Starch |
| --- | --- | --- | --- |
| 1st procedure | 0.24 | 0.26 | 0.27 |
| 2nd procedure | 0.26 | 0.23 | 0.25 |
| combined | 0.26 | 0.25 | 0.26 |

Example 6.

LARGE SCALE PRODUCTION OF ACYLATED STARCH PRODUCTS WITH ELEVATED LEVELS OF ACYLATION

The large scale procedure described in the first part of Example 6 was repeated but greater amounts of the anhydride (acetic, 120 g, propionic 164.4 g and butyric, 200 g) were used. The acylated starch products were recovered as described and analysed.

|  | Acetylated Starch | Butyrylated Starch | Propionylated Starch |
| --- | --- | --- | --- |
| Elevated acylation | 0.37 | 0.33 | 0.33 |

Example 7.

EXAMINING THE EFFECT OF ACYLATION ON THE RATE OF IN VITRO HYDROLYSIS.

Table 7 presents DS of the range of Acylated Starch products which have been prepared.

TABLE 7

DS of Acylated Starch products as determined by the titrimetric method

| Sample | Acetylated Starch | Butyrylated Starch | Propionylated Starch |
|---|---|---|---|
| 1 | 0.20 | 0.16 | 0.19 |
| 2 | 0.26 | 0.25 | 0.26 |
| 3 | 0.37 | 0.33 | 0.33 |

These materials were used to examine the effect of degree of substitution on the rate of hydrolysis with amylase. As previously (Example 2) the hydrolysis of the starches was followed using DNS reagent. These starch products will referred to in the following experiments as A1, A2, A3, B1, B2, B3, and P1, P1, P2, P3 for the batches of Acetylated-Butyrylated-, and Propionylated starch respectively.

Trial 1

1) Glucose (5 mg/ml) was dissolved in citrate buffer (pH 4.6) containing $CaCl_2$ (4 mM).
2) Dilutions were made to provide 1, 2, 3, 4 and 5 mg/mL standards to construct a calibration curve for the reducing equivalent determinations.
3) Control starch (starch which had gone through the sham treatment) was dissolved in citrate buffer at 5 mg/mL.
4) Acylated Starch products were dissolved in the citrate buffer (approx 100 mg/ 20 mL see table) after wetting with ethanol (0.2 mL). The samples were stirred overnight. This produced cloudy suspensions rather than clear solutions but when the enzyme was added the suspensions cleared very rapidly indicating that they were available to the enzyme.

TABLE 8

Amount of each Acylated Starch product weighed out to give equivalent to 100 mg/20 mL potential reducing equivalents from control starch.

| Sample | | % acyl group (w/w) | Wt equivalent (mg) |
|---|---|---|---|
| control | | 0.0 | 100.0 |
| Acetylated | A1 | 5.1 | 105.3 |
| Starch | A2 | 6.4 | 106.8 |
| | A3 | 9.1 | 110.0 |
| Butyrylated | B1 | 6.6 | 107.1 |
| Starch | B2 | 9.9 | 110.9 |
| | B3 | 12.9 | 114.8 |
| Propionylated | P1 | 6.4 | 106.8 |
| Starch | P2 | 8.5 | 109.3 |
| | P3 | 10.2 | 111.4 |

5) From each of the solutions 5 mL were transferred into 8 mL vials. Stir bars were added and 0.05 mL of α-amylase (Sigma) was added.
6) Aliquots (0.2 mL) was removed periodically (1, 5, 10, 20 min) and DNS reagent was added. The colour was developed and the absorbance (570 nm) was determined. The reducing equivalents were calculated.

Results

Table 9. Activity (release of reducing equivalents, mg glc) of α-amylase with Acylated Starch products as substrates.

TABLE 9

Activity (release of reducing equivalents, mg glc) of α-amylase with Acylated Starch products as substrates.

| Acylated Starch product | Time of sampling (min) | | | | |
|---|---|---|---|---|---|
| | 0 | 1 | 5 | 10 | 20 |
| A1 | 0.09 | 1.29 | 1.62 | 1.90 | 1.99 |
| A2 | 0.05 | 1.26 | 1.51 | 1.77 | 1.82 |
| A3 | 0.05 | 1.57 | 1.38 | 1.49 | 1.67 |
| B1 | 0.05 | 1.21 | 1.89 | 2.02 | 2.09 |
| B2 | 0.05 | 1.32 | 1.59 | 1.72 | 1.77 |
| B3 | 0.13 | 1.21 | 1.50 | 1.52 | 1.70 |
| P1 | 0.06 | 1.60 | 1.82 | 1.93 | 2.01 |
| P2 | 0.05 | 1.37 | 1.64 | 1.74 | 1.99 |
| P3 | 0.21 | 1.27 | 1.53 | 1.69 | 1.84 |
| Control | 0.10 | 2.34 | 2.36 | 2.38 | 2.56 |

Figure 3A:
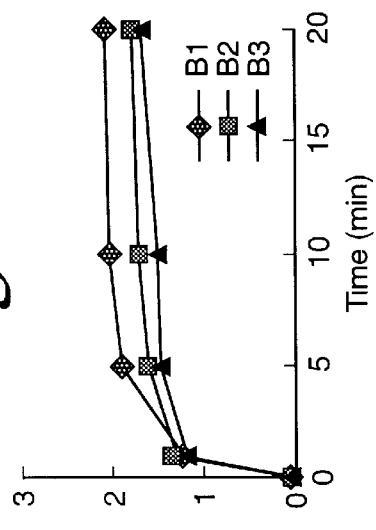
Figure 3C:
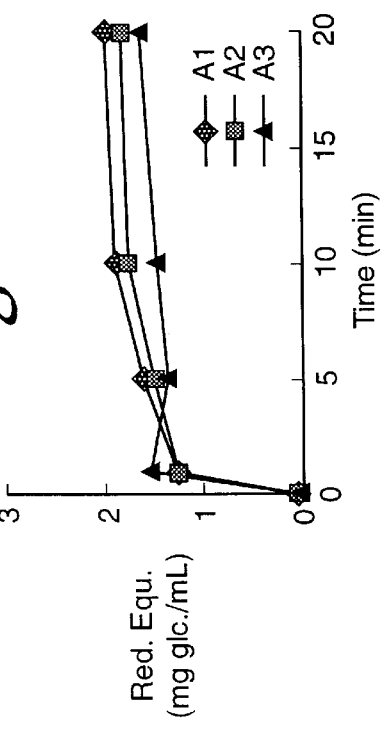
Figure 3B:
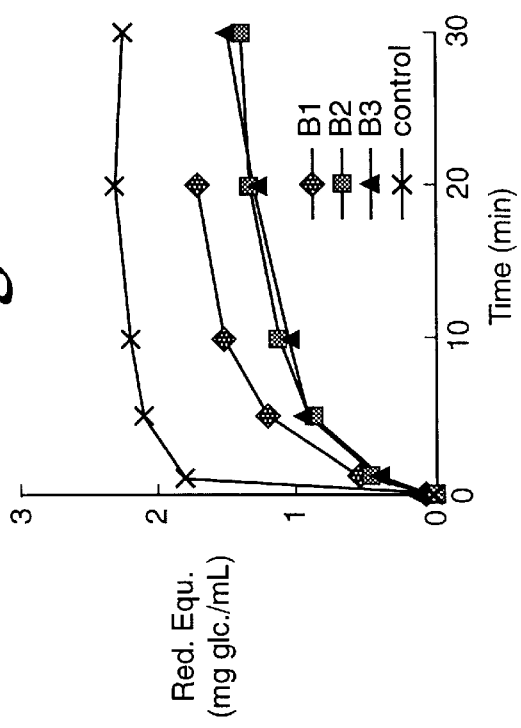

These data are shown in FIG. 3

Results

1) The acylated starch products were degraded less rapidly than the controls starch.
2) In all acylated starch products increasing the DS resulted in a slightly lower degradation rate.

Discussion

Clearly, the acylation of the starches inhibits hydrolysis by α amylase but there is no obvious difference between the Acylated Starch products. The effect of DS on the rates of hydrolysis is unexpectedly low. A possible reason for this is that enzyme concentration was much too high and the substrate was being overwhelmed by enzyme and steric hindrance caused by the acylation was not limiting the rate of hydrolysis.

Trial 2

The above experiment was repeated using Butyrylated Starch products only and a reduced amylase concentration.

1) Butyrylated Starch products (1, 2 and 3) (~100 mg, see previous Table for exact amount) were dissolved in citrate buffer (20 mL, pH4.6) by stirring for 2.5 h at 37° C.
2) α-Amylase (0.05 mL of a 1/10 dilution, Sigma chemicals) was added.
3) Aliquots (0.2 mL) of the reaction mixture were removed periodically and added to DNS reagent.
5) Colour was read and developed.

Results

The results from the treatment of control starch α-amylase and Butyrylated Starch products are presented in Table 13 below.

TABLE 10

Activity of α-amylase with Acylated Starch products as substrates

| Acylated Starch product | Time of sampling (min) | | | | | |
|---|---|---|---|---|---|---|
| | 0 | 1 | 5 | 10 | 20 | 30 |
| B1 | 0.00 | 0.54 | 1.19 | 1.51 | 1.70 | |
| B2 | 0.00 | 0.42 | 0.88 | 1.11 | 1.30 | 1.38 |
| B3 | 0.14 | 0.45 | 0.90 | 1.06 | 1.29 | 1.47 |
| control | 0.01 | 1.81 | 2.10 | 2.19 | 2.28 | 2.23 |

Figure 4:
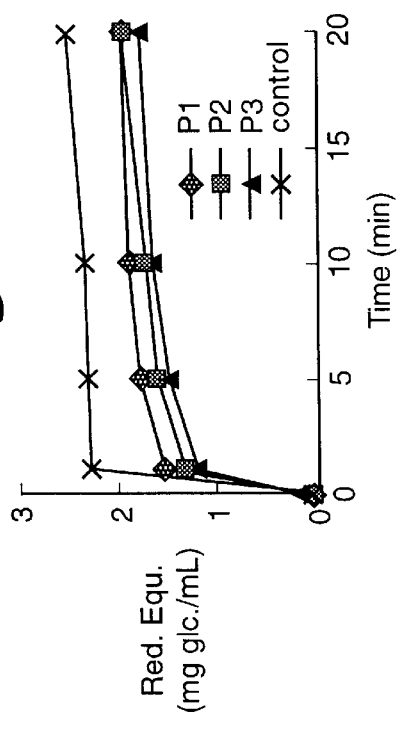

These data are shown in graphic form in FIG. 4.

Results

The data in Table 10 and FIG. 4 demonstrate that increasing the DS of Butyrylated Starch decreased the rate of hydrolysis of the starch. Butyrylated Starch B1 (DS 0.16)

was hydrolysed faster that B2 and B3 but not as fast as the control starch. There was no difference between B2 and B3.

Discussion

Reducing the enzyme concentration demonstrated that the DS can be used to influence the susceptibility of starch to α amylases (and hence its potential digestibility). If the enzyme concentration is reduced even further it may be possible to distinguish between Butyrylated Starch B2 and B3. The data from the experiment also suggest that the endpoint of the reaction is reduced by the acylation. In other words, some of the starch remains unavailable to the amylase enzyme. This suggests that the organic acids completely protect some of the starch molecule from degradation.

Example 8.

NUTRITIVE EFFECTS OF FEEDING RATS ACYLATED STARCH.

Large amounts (~500 g) of Acetylated Starch, Butyrylated Starch and Propionylated Starch were prepared by the large scale procedures detailed in Example 6 above. In order to examine their nutritive activity the following experiment was carried Out.

Method

Diets containing the Acetylated-, Butyrylated- and Propionylated Starch and a control starch were fed to 4 groups of 8 rats for 14 days. Degree of substitution were as follows (acetate DS 0.20, propionate DS 0.16, butyrate DS 0.19). The composition of the diets is shown in the table

TABLE 11

Composition of trial diets

| Ingredient | Composition (g/kg) |
|---|---|
| casein | 200.0 |
| methionine | 1.5 |
| sucrose | 50.0 |
| starch | 401.5 |
| corn oil | 100.0 |
| mineral mix | 35.0 |
| vitamin mix | 10.0 |
| choline tartrate | 2.0 |
| cellulose | 50.0 |
| Acylated Starch or control starch* | 150.0 |

The diets were cold extruded into pellets, dried and stored at low temperature prior to feeding.

Rat Husbandry 1) 40 Rats were held in group cages and fed commercial rat food.
2) Rats were randomly allocated to 4 treatment equal live weight groups of 8 animals (8 animals being culled) and fed the experimental diets for 14 days.
3) Feed consumption was monitored daily during the experiment.
4) Individual rat weights were determined periodically (each 2–days).

Sample collection

1) The rats were anaesthetised and bled from the aorta and the portal vein. The animals were killed by rupture of the diaphragm.
2) The caecal, proximal colon and distal colon contents were collected.

Results

Rat Husbandry

Feed consumption and weight gain data are shown in Table 12. There was no significant effect of diet on weight gain. As individual feed consumption was not monitored, differences between groups could not be tested significantly. There was considerable feed spillage for rats fed the control diet.

TABLE 12

Individual body weight gain and group feed consumption data from rats fed Acylated Starch products.

| Diet | Rat Weight gain (g) | Group Feed Consumption (g) |
|---|---|---|
| control | 79 (8)[1] | 3469 |
| Acetylated Starch | 67 (4) | 2753 |
| Propionylated Starch | 73 (3) | 3221 |
| Butyrylated Starch | 65 (2) | 2803 |

[1]Mean values with standard errors, in brackets, are shown.

Large Bowel SCFA levels

Caecum. The levels of SCFA in the caeca of rats fed the Acylated Starch products and the pool sizes are shown in Table 17 and 18 and FIGS. 5 and 6

TABLE 13

SCFA levels in the caeca of rats fed the control starch and the Acylated Starch products.

| | SCFA (mM/L) | | | |
|---|---|---|---|---|
| | Acetate | Propionate | Butyrate | Total SCFA |
| Control | 22.0[a] | 7.2[a] | 4.7[a] | 33.9[a] |
| | (1.0) | (0.3) | (0.2) | (1.3) |
| Acetylated Starch | 47.71[c] | 13.9[c] | 7.3[b] | 68.8[c] |
| | (2.0) | (0.6) | (0.7) | (2.9) |
| Propionylated Starch | 33.9[b] | 30.9[d] | 8.3[b] | 73.0[c] |
| | (0.9) | (1.0) | (0.3) | (2.0) |
| Butyrylated Starch | 34.85[b] | 11.1[b] | 28.5[c] | 74.4[c] |
| | (1.9) | (0.4) | (1.3) | (2.0) |

[1]Means (n = 8) with standard errors in brackets
[a,b,c,d]Values with unlike superscripts are significantly different (P < 0.01)

Figure 5:
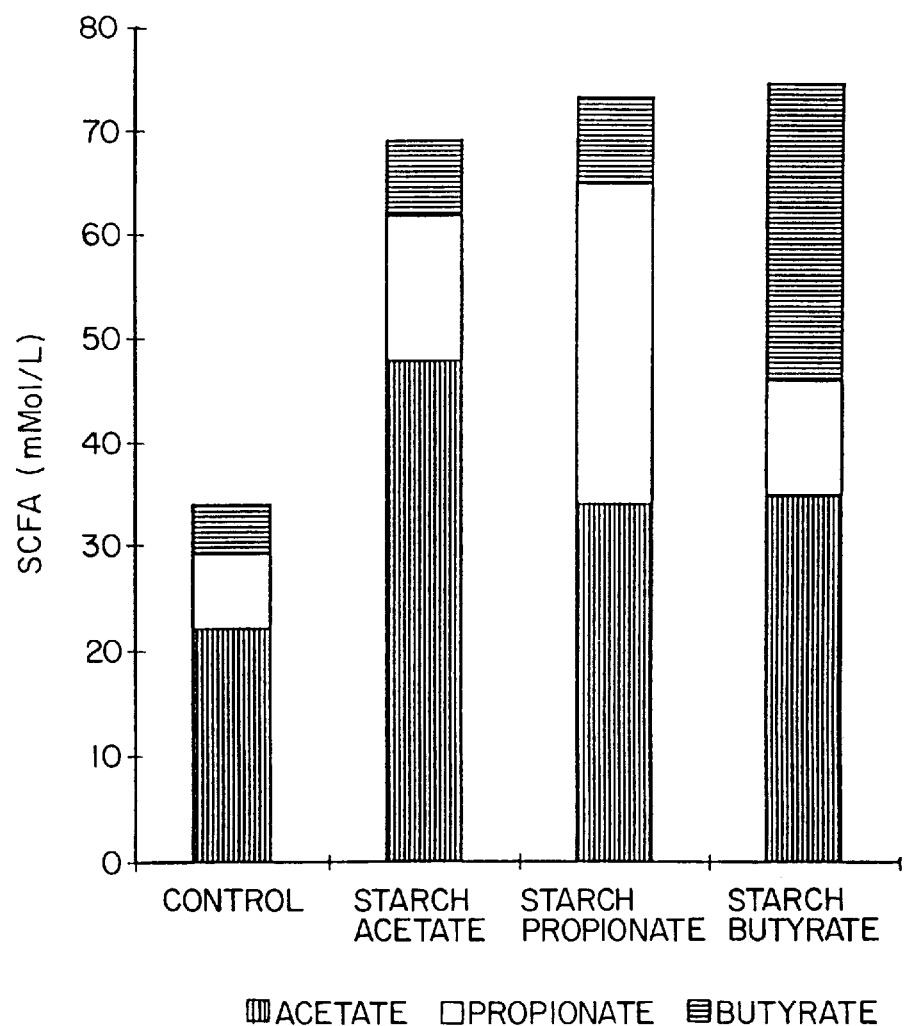

These results are shown graphically in FIG. 5.

TABLE 12

SCFA pools in the caeca of rats fed the control starch and the Acyl Starch products.

| | SCFA (mmols) | | | |
|---|---|---|---|---|
| | Acetate | Propionate | Butyrate | Total SCFA |
| Control | 37.1[a] | 12.1[a] | 8.1[a] | 57.4[a] |
| | (3.0) | (1.0) | (0.8) | (4.8) |
| Acetylated Starch | 142.0[c] | 41.2[b] | 20.7[b] | 203.8[b] |
| | (10.0) | (2.7) | (2.1) | (14.4) |
| Propionylated Starch | 104.2[b] | 95.6[c] | 25.6[b] | 225.5[b] |
| | (7.8) | (8.1) | (1.9) | (17.7) |
| Butyrylated Starch | 115.7[b] | 36.7[b] | 93.1[c] | 245.1[b] |
| | (11.0) | (2.3) | (6.1) | (17.2) |

[1]Means (n = 8) with standard errors in brackets
[a, b, c]Values with unlike superscripts are significantly different (P < 0.01)

Figure 6:
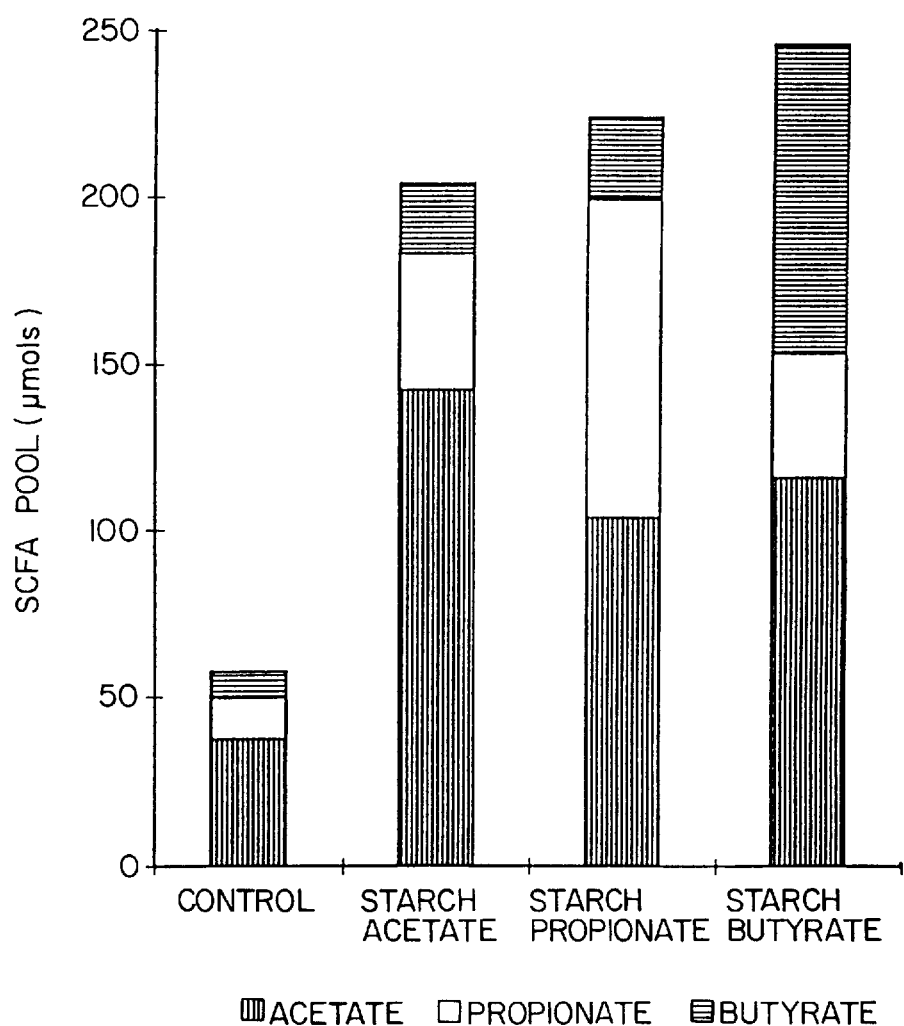

These data are represented graphically in FIG. 6.

Distal Colon

The SCFA concentrations and pool sizes are presented in Tables 13 and 14 and in FIGS. 7a,b and 12a,b.

TABLE 13

SCFA levels in the distal colon of rats fed Acylated Starch products.

| | SCFA (mmol/L) | | | |
|---|---|---|---|---|
| | Acetate | Propionate | Butyrate | Total SCFA |
| Control | 13.7$^a$ | 2.8$^a$ | 1.3$^a$ | 17.7$^a$ |
| | (0.4) | (0.1) | (0.2) | (0.5) |
| Acetylated Starch | 30.1$^d$ | 10.9$^c$ | 4.9$^b$ | 45.8$^c$ |
| | (1.7) | (0.8) | (0.6) | (2.4) |
| Propionylated Starch | 24.6$^c$ | 17.2$^d$ | 3.7$^b$ | 45.5$^c$ |
| | (1.4) | (0.7) | (0.3) | (2.2) |
| Butyrylated Starch | 20.6$^b$ | 6.8$^c$ | 10.6$^c$ | 38.1$^b$ |
| | (0.8) | (0.6) | (1.0) | (1.1) |

$^1$Means (n = 8) with standard errors in brackets
$^{a,b,c,d}$Values with unlike superscripts are significantly different (P < 0.01)

Figure 7:
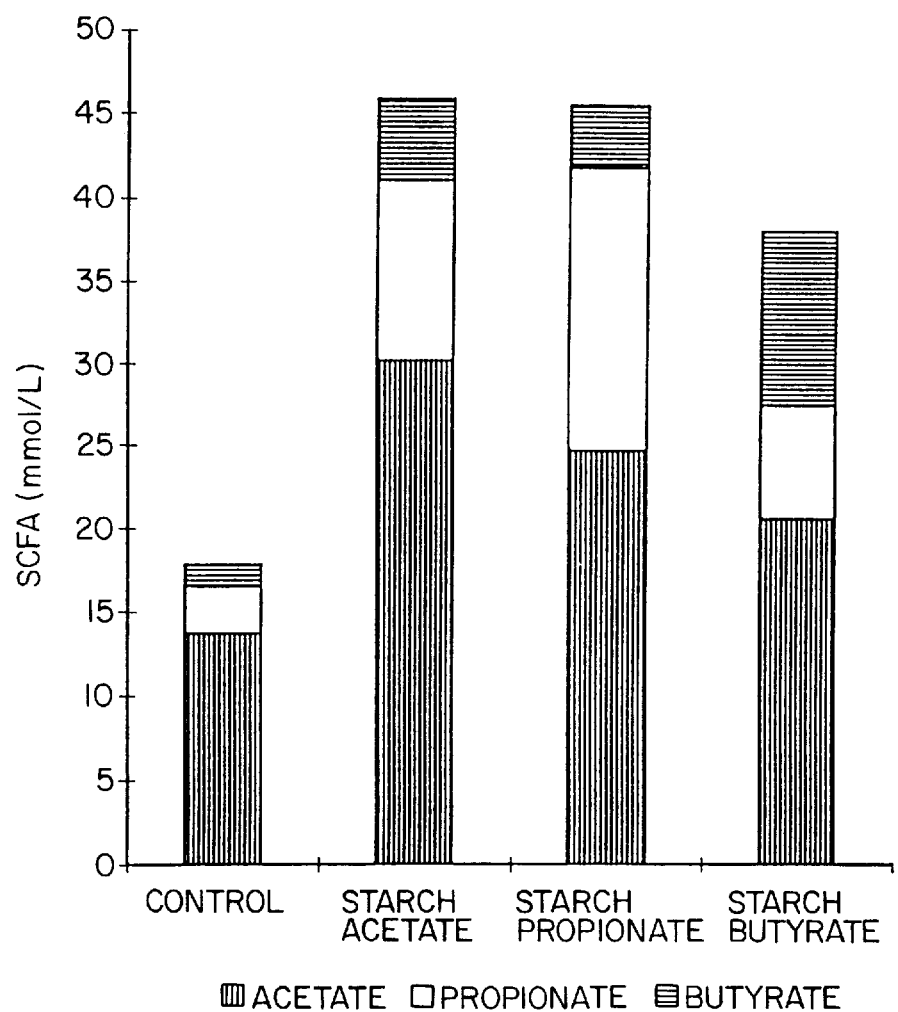

This data is represented graphically in FIG. 7.

TABLE 14

SCFA pools in the distal colon of rats fed the control starch and the Acylated Starch products.

| | SCFA (mmols) | | | |
|---|---|---|---|---|
| | Acetate | Propionate | Butyrate | Total SCFA |
| Control | 6.78$^a$ | 1.38$^a$ | 0.63$^a$ | 8.79$^a$ |
| | (0.65) | (0.16) | (0.08) | (0.82) |
| Acetylated Starch | 27.78$^c$ | 10.01$^c$ | 4.53$^b$ | 42.31$^c$ |
| | (1.9) | (0.87) | (0.63) | (2.94) |
| Propionylated Starch | 20.65$^b$ | 14.5$^d$ | 3.11$^b$ | 38.34$^{bc}$ |
| | (1.8) | (1.36) | (0.35) | (3.41) |
| Butyrylated Starch | 17.48$^b$ | 5.58$^b$ | 8.84$^c$ | 32.09$^b$ |
| | (1.53) | (0.61) | (0.79) | (2.33) |

$^1$Means (n = 8) with standard errors in brackets
$^{a,b,c,d}$Values with unlike superscripts are significantly different (P < 0.01)

Figure 8:
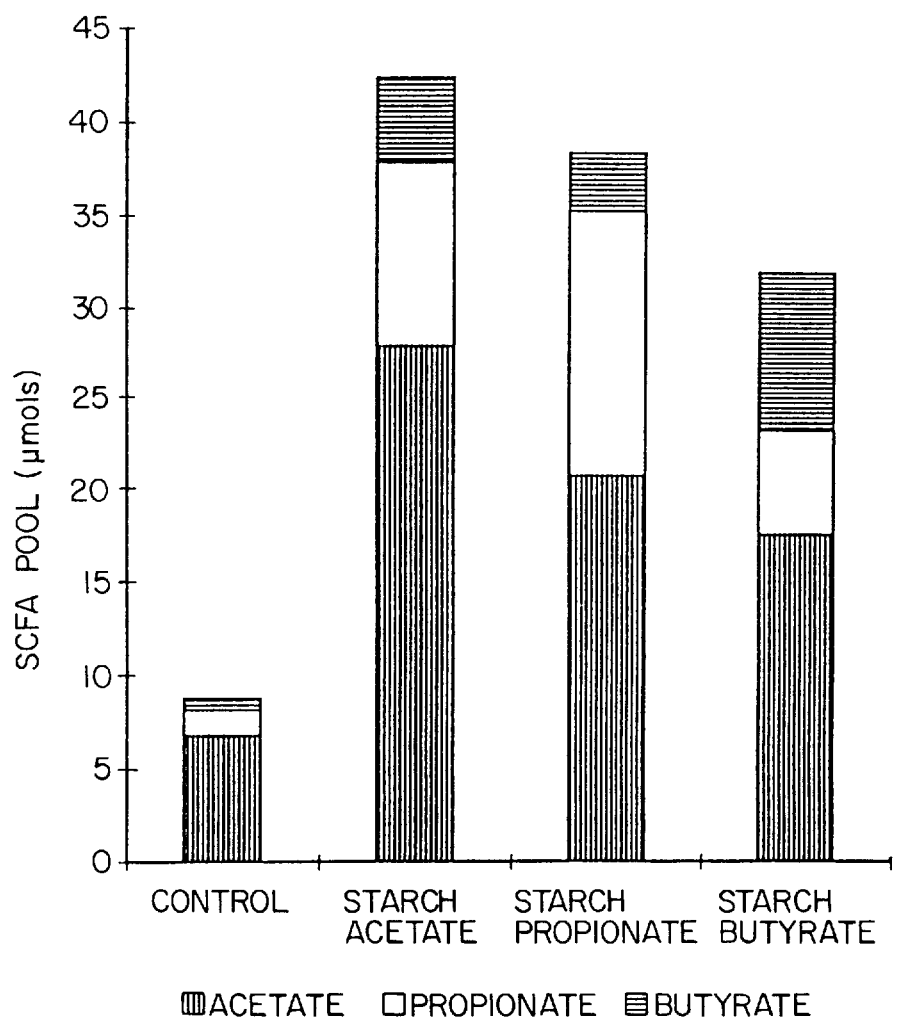

This data is represented graphically in FIG. 8.

If it is assumed that the acylation of each of the Acylated Starch products confers the same degree of protection to digestion in the small intestine (which is likely as the DS of the products is about the same and the results of the in vitro studies suggest it) the amount of SCFA originating directly from the acyl substituent (rather than from increased fermentation) can be estimated.

For example in the in the caecum acetate conc Acetylated Starch.from direct release=acetate conc.Acetylated Starch−(acetate conc.Propionylated Starch+acetate conc.Butyrylated Starch)/2=47.7375−(33.85+34.85)/2=13.39 mmol/L This amount can then be subtracted from the total amounts of each of the SCFA to give a measure of the SCFA derived from fermentation.

This calculation has been done for each of the three sections and the results are in the Table 15

TABLE 15

Estimated contribution to SCFA levels in the hindgut of rats fed Acylated Starch products derived directly from the acyl sidechains

| Section | Acetate | Propionate | Butyrate |
|---|---|---|---|
| Caecum - | | | |
| -conc. (mmol/L) | 13.39 | 18.39 | 20.68 |
| - pool (mmol) | 32.05 | 56.95 | 70.0 |

TABLE 15-continued

Estimated contribution to SCFA levels in the hindgut of rats fed Acylated Starch products derived directly from the acyl sidechains

| Section | Acetate | Propionate | Butyrate |
|---|---|---|---|
| Distal colon | | | |
| - conc. (mmol/L) | 7.75 | 8.35 | 6.34 |
| - pool (mmol) | 8.71 | 6.68 | 5.06 |

Hind Gut Starch

The amount of starch in the caecal and distal colon samples was determined using a method detailed elsewhere. The method involves treatment of the samples with base to saponify the Acylated Starch products. Thus the method determines the total starch in the sample.

Results

Figure 9:
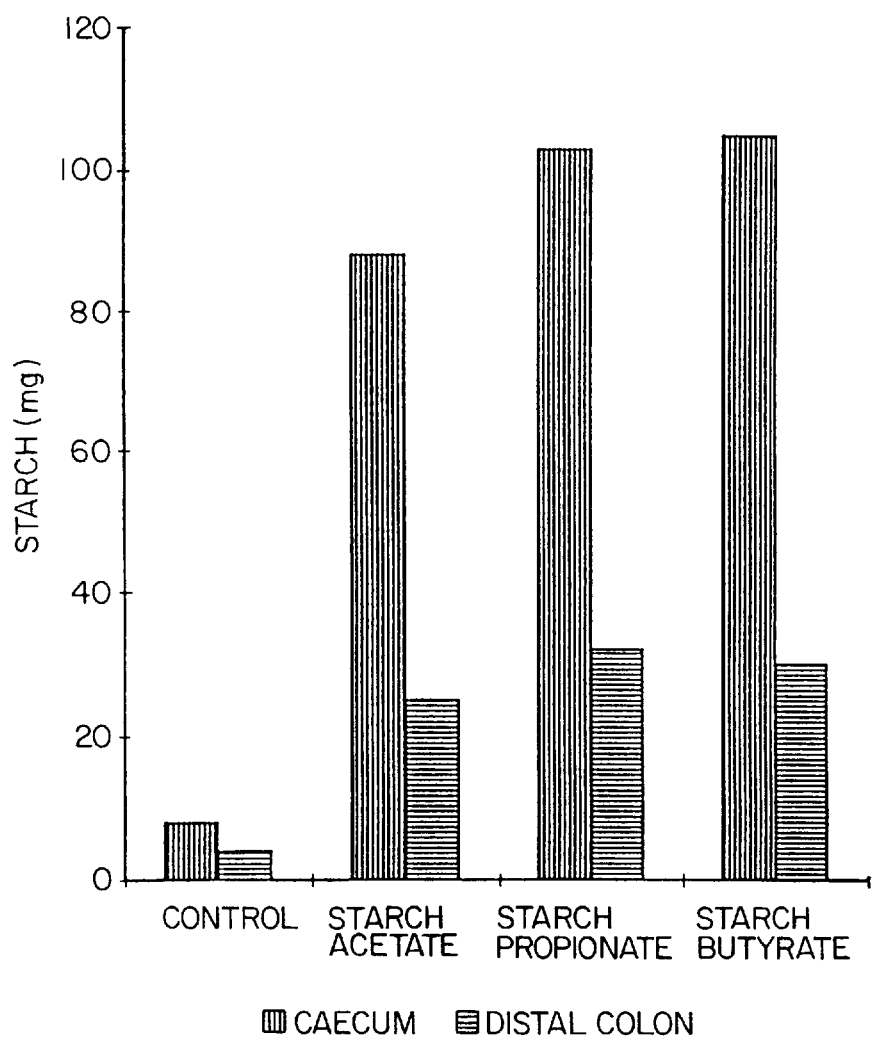

The amounts of starch in the caecum and distal colon are presented in Table 16, and FIG. 9.

TABLE 16

Amounts of starch (mg) in the caecum and distal colon of rats fed the Acylated Starch products.

| | Total Starch (mg) | |
|---|---|---|
| | Caecum | Distal Colon |
| Control | 8$^a$ | 4$^a$ |
| | (1) | (0.2) |
| Acetylated Starch | 88$^b$ | 25$^b$ |
| | (6) | (3) |
| Propionylated Starch | 103$^b$ | 32$^b$ |
| | (14) | (4) |
| Butyrylated Starch | 105$^b$ | 30$^b$ |
| | (11) | (5) |

Means (n = 8) with standard errors in brackets
$^{a,b}$Values with unlike superscripts are significantly different (P < 0.01)

These data are represented graphically in FIG. 9.

Discussion

The data from the feeding trial detailed above confirms that acylated starch products can be used to manipulate the levels of SCFA along the colon. The effect is achieved through two mechanisms. Firstly the SCFA protect the starch from digestion in the small intestine. This is clearly indicated by the much higher levels of starch which were detected in the colonic contents from rats fed the Acylated Starch products. The increase in flow of fermentable material (starch) into the hindgut results in an increase in the level of all SCFA in rats fed acylated Starch products compared to the rats fed the control starch. In addition there is a direct release of the SCFA from the acylated products in the hindgut which results in increases in specific SCFA levels. The acylated Starch products also cause dramatic increases in faecal bulk and moisture content and also give a significant drop in pH value as can be seen in the data shown in Tables 17, 18 and 19.

TABLE 17

Weights of caecal, proximal and distal colon contents of rats fed starch products

| Diet | Caecum | Proximal colon | Distal colon |
|---|---|---|---|
| Control | 2.17$^a$ | 0.66 | 0.98 |
| | (0.41) | (0.28) | (0.17) |

TABLE 17-continued

Weights of caecal, proximal and distal colon contents of rats fed starch products

| Diet | Caecum | Proximal colon | Distal colon |
|---|---|---|---|
| Acetylated Starch | 3.82[b] (0.83) | 1.10 (0.47) | 1.44 (0.13) |
| Propionylated Starch | 3.97[b] (0.77) | 1.15 (0.28) | 1.36 (0.35) |
| Butyrylated Starch | 4.26[b] (0.74) | 1.11 (0.57) | 1.31 (0.33) |

[1]Means (n = 8) with standard errors in brackets
[a,b]Values with unlike superscripts are significantly different (P < 0.05)

Feeding esterified starches caused a significant increase in caecal content independent of the nature of the SCFA moiety that was due to greater solids rather than increased moisture. Whilst there was a tendency for proximal and distal colon content to increase it did not reach significance.

TABLE 18

Moisture content (%) of colonic digesta of rats fed starch products

| Diet | Caecum | Proximal colon | Distal colon |
|---|---|---|---|
| Control | 77.6 (1.3) | 75.3 (5.0) | 49.9[a] (3.3) |
| Acetylated Starch | 78.4 (1.5) | 79.5 (1.9) | 63.8[b] (1.8) |
| Propionylated Starch | 77.5 (1.3) | 78.7 (2.4) | 65.2[b] (3.2) |
| Butyrylated Starch | 77.1 (1.6) | 77.5 (2.4) | 65.2[b] (3.2) |

[1]Means (n = 8) with standard errors in brackets
[a,b]Values with unlike superscripts are significantly different (P < 0.05)

TABLE 19 pH of colonic contents of rats fed starch products

| Diet | Caecum | Proximal colon | Distal colon |
|---|---|---|---|
| Control | 7.63[a] (0.09) | 7.41[a] (0.10) | 6.94[a] (0.17) |
| Acetylated Starch | 6.00[b] (0.14) | 6.12[b] (0.15) | 6.13[b] (0.15) |
| Propionylated Starch | 6.15[b] (0.18) | 6.30[b] (0.14) | 6.10[b] (0.14) |
| Butyrylated Starch | 6.19[b] (0.10) | 6.39[b] (0.18) | 6.18[b] (0.17) |

[1]Means (n = 8) with standard errors in brackets
[a,b]Values with unlike superscripts in a column are significantly different (P < 0.05)

There is a significant fall in pH in the caeca of all animals fed the acylated starches which continued through the entire large bowel indicative of increased SCFA concentration and fermentative activity.

CONCLUSIONS

It is therefore possible to prepare acylated starches with different DS in a controlled manner in the laboratory on a large scale.

Preliminary experiments indicate that acylation inhibits the action of both amyloglucosidase and α-amylase. Increasing the DS increases the enzyme inhibition.

The acylated starch products are resistant to digestion in the small intestine and hence are a form of Resistant Starch. Very large differences (10 fold) in both SCFA concentrations and pool sizes can be achieved by feeding the acylated Starch products. The Acylated Starch products can be used to specifically and predictably alter the levels of SCFA in the hindgut.

Example 9.
PREPARATION OF ACYLATED CARRIERS OTHER THAN STARCH

Methods for preparation of SCFA linked to Non Starch Polysaccharides are generally the same as for the preparation of SCFA linked to Starches. A number of different methods are available. For large scale preparation expensive solvents such as DMSO are not favoured and direct acylation is preferred with the SCFA anhydride. Several methods for acylation that can be used are described in Albrecht and Rau (1994) in Carbohydrate Polymers 24; 193–197, and references therein which references are incorporated herein.

Example 10.
PREPARATION OF A FOOD PRODUCT

Generally where it is desired to have a regime of preventative intake of SCFA then the SCFA linked to carbohydrate is perhaps best included in a solid food. In this instance there is no criticality as to which carbohydrate is used other than for the varying effect it might have in the large bowel. The food product may for example be a bread, and where an acylated starch is used there might be a 10% substitution for flour. The formulation might therefore be as follows:

| Flour | 90 parts |
|---|---|
| Acylated Starch | 10 parts |
| Fat | 2 parts |
| salt | 2 parts |
| Improver | 1 part |
| Yeast | 2.5 parts |

The production of the bread is using a rapid dough technique, as is known to those skilled in the art.

Example 11.
PREPARATION FOR PHARMACEUTICAL TREATMENTS

The use of a food product to deliver the SCFA to the large bowel is beneficial however the drawback is that there is no means of accurately determining the level of SCFA that is administered, because it seems that from the literature that the availability of the SCFA in the large colon will not only vary with the bond and degree of substitution with its particular carrier molecule, but also with the quality and quantity of constituents of the food in which it is incorporated. For the purpose of maintaining a relatively even level of SCFA in the large bowel, an direct oral intake is preferable. This is preferably in the form of a powdered formulation, but may also be in the form of a liquid formulation.

One formulation for a pharmaceutical that may be solubilized in with water and then ingested is as follows:

| Psyllium | 30 parts |
|---|---|
| Acylated Psyllium | 50 parts |
| Fructooligosaccharide | 20 parts |

This formulation would be made by approved methods. The formulation may be changes so as to, for example substitute a Butyrylated starch form the acetylatedpsyllium, and guar gum for the Psyllium.

It is anticipated that a measured dose would be solubilized in water and ingested.

It is to be understood that other formulations as can be formulated by those skilled in the pharmaceutical industry can be prepared and used, for example, a tablet form may be desired.

The level of intake will vary upon the condition that is to be treated, and some indications can be gathered from the literature of previous attempts at treatments. For example butyrate enemas have been used for the treatment of distal Ulcerative colitis, administering 100 mmol/L of a 2 week period. Scheppach et al in Gastroenterology (1992) 103; 51–56, which reference and references therein related to effective SCFA levels are incorporated into this specification. It is anticipated that similar concentrations of butyrate should be achieved by oral administration to treat Colitis, although the presence of other SCFAs may lower the level of Butyrate required to be effective. As is apparent with Colitis other SCFA's may also have an effect, and it may in fact be preferred to administer one or more of the SCFA's in combination.

We claim:

1. A method of delivering a fatty acid to the colon of a human or animal, including the step of ingesting a physiologically acceptable level of an agent, said agent comprising a carrier covalently bonded to the fatty acid by a bond hydrolysable in the colon to give free fatty acid.

2. The method of claim 1 wherein the fatty acid is a short chain fatty acid (SCFA).

3. The method of claim 2 wherein the carrier is a carbohydrate.

4. The method of claim 3 wherein the carrier is soluble.

5. The method in claim 3 wherein the carbohydrate is a non starch polysaccharide selected from the group consisting of pectin, inulin, cellulose, hemicellulose, oligosaccharides and gums.

6. The method as in claim 5 wherein the carbohydrate is a pectin selected from the group consisting of high, medium and low methoxylated pectins and high, medium and low gel strength pectins and pectins derived from oranges, lemons or apples.

7. The method in claim 5 wherein the carbohydrate is a cellulose selected from the group consisting of microcrystalline cellulose, methyl cellulose, hydroxypropylmethyl cellulose and carboxymethyl cellulose.

8. The method in claim 5 wherein the carbohydrate is an oligosaccharide selected from the group consisting of fructooligosaccharides, galactooligosaccharides and maltodextrins.

9. The method of claims 5 wherein the carbohydrate is a gum selected from the group consisting of guar arabic, xantham, tragacanth, locust bean and psyllium.

10. The method of claim 3 wherein the carbohydrate is a starch.

11. The method of claim 10 wherein the starch is a starch digestible in the small intestine.

12. The method as in claim 10 wherein the starch is a starch resistant to digestion in the small intestine.

13. The method as in claim 10 wherein the starch is a native starch.

14. The method as in claim 13 where the native starch is derived from a material selected from the group consisting of wheat, potato, tapioca, maize, rice and oat.

15. The method as in claim 10 wherein the starch is a modified starch.

16. The method as in claim 15 wherein the starch is modified through the use of any one or more of the following, heat and/or moisture, physically, enzymatically, chemical hydrolysis, esterification, oxidation, cross bonding with difunctional reagents, and carboxymethylation.

17. The method as in claim 1 wherein the bond is either an ester bond or an amide bond.

18. The method as in claim 2 wherein the SCFA is selected from the group consisting of acetate, propionate, butyrate, and branched or modified derivatives thereof.

19. The method as in claim 2 wherein the SCFA is acetate.

20. The method as in claim 2 wherein the SCFA is propionate.

21. The method as in claim 2 wherein the SCFA is butyrate.

22. The method as in claim 3 wherein the degree of substitution ranges from 0.05 acyl group per saccharide unit to 2 acyl groups per saccharide unit.

23. The method as in claim 3 wherein the degree of substitution ranges from 0.1 acyl groups per saccharide unit to 0.5 acyl group per saccharide unit.

24. A method of lowering the risk of a colon disorder in humans or animals, comprising the step of administering a pharmacologically effective and physiologically acceptable level of an agent, said agent comprising a carrier covalently bonded with a fatty acid by a bond that is hydrolysable in the colon to give free fatty acid.

25. The method of claim 24, wherein the fatty acid is a short chain fatty acid (SCFA).

26. The method of claim 25 wherein the colon disorder is selected from the group consisting of diverticulitis, colonic cancer, constipation, colitis, irritable bowel and diarrhoea.

27. The method of claim 26 wherein the carrier is a carbohydrate.

28. The method of claim 27 wherein the carrier is soluble.

29. The method in claim 27, wherein the carbohydrate is a non starch polysaccharide selected from the group consisting of pectin, inulin, cellulose, hemicellulose, oligosaccharides, and gums.

30. The method as in claim 29 wherein the carbohydrate is a pectin selected from the group consisting of high, medium and low methyoxylated pectins and high, medium and low gel strength pectins and pectins derived from oranges, lemons or apples.

31. The method in claim 29, wherein the carbohydrate is a cellulose selected from the group consisting of microcrystalline cellulose, methyl cellulose, hydroxypropylmethyl cellulose and carboxymethyl cellulose.

32. The method in claim 29 wherein the carbohydrate is an oligosaccharide selected from the group consisting of fructooligosaccharides, galactooligosaccharides and maltodextrins.

33. The method of claim 29, wherein the carbohydrate is a gum selected from the group consisting of guar, arabic, xantham, tragacanth, locust bean and psyllium.

34. The method of claim 27 wherein the carbohydrate is a starch.

35. The method of claim 34 wherein the starch is a starch digestible in the small intestine.

36. The method as in claim 34 wherein the starch is a starch resistant to digestion in the small intestine.

37. The method as in claim 34 wherein the starch is a native starch.

38. The method as in claim 37 where the native starch is derived from a material selected from the group consisting of wheat, potato, tapioca, maize, rice and oat.

39. The method as in claim 34 wherein the starch is a modified starch.

40. The method as in claim 39 wherein the starch is modified through the use of any one or more of the following, heat and/or moisture, physically, enzymatically, chemical hydrolysis, esterification, oxidation, cross bonding with difunctional reagents, and carboxymethylation.

41. The method as in claim 25 wherein the bond is either an ester bond or an amide bond.

42. The method as in claim 25 wherein the SCFA is selected from the group consisting of acetate, propionate, butryate, and branched or modified derivatives thereof.

43. The method as in claim 25 wherein the SCFA is acetate.

44. The method as in claim 25 wherein the SCFA is propionate.

45. The method as in claim 25 wherein the SCFA is butyrate.

46. The method as in claim 27 wherein the degree of substitution ranges from 0.05 acyl group per saccharide unit to 2 acyl groups per saccharide unit.

47. The method as in claim 27 wherein the degree of substitution ranges from 0.1 acyl groups per saccharide unit to 0.5 acyl group per saccharide unit.

48. A method of treating or alleviating the effects of a colonic disorder in humans or animals, comprising the step of administering a pharmacologically effective and physiologically acceptable level of an agent, said agent comprising a carrier covalently bonded with a fatty acid by a bond hydrolysible in the colon to give free fatty acid.

49. The method of claim 48 wherein the fatty acid is a short chain fatty acid (SCFA).

50. The method of claim 49, wherein the colonic disorder is selected from the group consisting of colonic cancer, diverticulitis, constipation, irritable bowel and colitis.

51. The method of claim 50 wherein the carrier is a carbohydrate.

52. The method of claim 51 wherein the carrier is soluble.

53. The method in claim 50 wherein the carbohydrate is a non starch polysaccharide selected from the group consisting of pectin, inulin, cellulose, hemicellulose, oligosaccharides and gums.

54. The method as in claim 53 wherein the carbohydrate is a pectin selected from the group consisting of high, medium and low methoxylated pectins and high, medium and low gel strength pectins and pectins derived from oranges, lemons or apples.

55. The method in claim 53 wherein the carbohydrate is a cellulose selected from the group consisting of microcrystalline cellulose, methyl cellulose, hydroxypropylmethyl cellulose and carboxymethyl cellulose.

56. The method in claim 53 wherein the carbohydrate is an oligosaccharide selected from the group consisting of fructooligosacchrides, galactooligosaccharides and maltodextrins.

57. The method of claim 53 wherein the carbohydrate is a gum selected from the group consisting of guar, arabic, xantham, tragacanth, locust bean and psyllium.

58. The method of claim 51 wherein the carbohydrate is a starch.

59. The method of claim 58 wherein the starch is a starch digestible in the small intestine.

60. The method as in claim 58 wherein the starch is a starch resistant to digestion in the small intestine.

61. The method as in claim 58 wherein the starch is a native starch.

62. The method as in claim 61, where the native starch is derived from a material selected from the group consisting of wheat, potato, tapioca, maize, rice and oat.

63. The method as in claim 58 wherein the starch is a modified starch.

64. The method as in claim 63 wherein the starch is modified through the use of any one or more of the following, heat and/or moisture, physically, enzymatically, chemical hydrolysis, esterification, oxidation, cross bonding with difunctional reagents, and carboxymethylation.

65. The method as in claim 49 wherein the bond is either an ester bond or an amide bond.

66. The method as in claim 49 wherein the SCFA is selected from the group consisting of acetate, propionate, butryate, and branched or modified derivatives thereof.

67. The method as in claim 49 wherein the SCFA is acetate.

68. The method as in claim 49 wherein the SCFA is propionate.

69. The method as in claim 49 wherein the SCFA is butyrate.

70. The method as in claim 51 wherein the degree of substitution ranges from 0.05 acyl group per saccharide unit to 2 acyl groups per saccharide unit.

71. The method as in claim 51 wherein the degree of substitution ranges from 0.1 acyl groups per saccharide unit to 0.5 acyl group per saccharide unit.

72. A pharmaceutical agent for delivering fatty acid to the colon of humans and animals said agent comprising a carrier covalently bonded to the fatty acid by a bond that is hydrolysable in the colon to give free fatty acid said agent carried in a pharmaceutically acceptable form.

73. The pharmaceutical agent of claim 72 wherein the fatty acid is a short chain fatty acid (SCFA).

74. The pharmaceutical agent of claim 73 wherein the carrier is a carbohydrate.

75. The pharmaceutical agent of claim 74 wherein the carrier is water soluble.

76. The pharmaceutical agent in claim 74 wherein the carbohydrate is a non starch polysaccharide selected from the group consisting of pectin, inulin, cellulose, hemicellulose, oligosaccharides and gums.

77. The pharmaceutical agent as in claim 76 wherein the carbohydrate is a pectin selected from the group consisting of high, medium and low methoxylated pectins and high, medium and low gel strength pectins and pectins derived from oranges, lemons or apples.

78. The pharmaceutical agent in claim 76 wherein the carbohydrate is a cellulose selected from the group consisting of microcrystalline cellulose, methyl cellulose, hydroxypropylemethyl cellulose and carboxymethyl cellulose.

79. The pharmaceutical agent in claim 76 wherein the carbohydrate is an oligosaccharide selected from the group consisting of fructooligosacchrides, galactooligosaccharides and maltodextrins.

80. The pharmaceutical agent of claim 76 wherein the carbohydrate is a gum selected from the group consisting of guar, arabic, xantham, tragacanth, locust bean, and psyllium.

81. The pharmaceutical agent of claim 74 wherein the carbohydrate is a starch.

82. The pharmaceutical agent of claim 81 wherein the starch is a starch digestible in the small intestine.

83. The pharmaceutical agent as in claim 81 wherein the starch is a starch resistant to digestion in the small intestine.

84. The pharmaceutical agent as in claim 81 wherein the starch is a native starch.

85. The pharmaceutical agent as in claim 84 wherein the native starch is derived from a group consisting of wheat, potato, tapioca, maize, rice and oat.

86. The pharmaceutical agent as in claim 81 wherein the starch is a modified starch.

87. The pharmaceutical agent as in claim 86 wherein the starch is modified through the use of any one or more of the following, heat and/or moisture, physically, enzymatically, chemical hydrolysis, esterification, oxidation, cross bonding with difunctional reagents, and carboxymethylation.

88. The pharmaceutical agent as in claim 72 wherein the bond is either an ester bond or an amide bond.

89. The pharmaceutical agent as in claim 73 wherein the SCFA is selected from the group consisting of acetate, propionate, butyrate, and branched or modified derivatives thereof.

90. The pharmaceutical agent as in claim 73 wherein the SCFA is acetate.

91. The pharmaceutical agent as in claim 73 wherein the SCFA is propionate.

92. The pharmaceutical agent as in claim 73 wherein the SCFA is butryate.

93. The pharmaceutical agent as in claim 74 wherein the degree of substitution ranges from 0.05 acyl group per saccharide unit to 2 acyl groups per saccharide unit.

94. The pharmaceutical agent as in claim 74 wherein the degree of substitution ranges from 0.1 acyl groups per saccharide unit to 0.5 acyl group per saccharide unit.

95. A method of preparing an agent for delivering fatty acid to the colon of humans and animals, said agent comprising a carrier covalently bonded to the fatty acid by a bond hydrolysable in the colon to give free fatty acid, said method including the step of determining an appropriate average degree of substitution of carrier with the fatty acid, and the step of acylating the carrier with said fatty acid at the average degree of substitution so determined.

96. The method of claim 95 wherein the fatty acid is a short chain fatty acid (SCFA).

97. The method of claim 96 wherein the carrier is a carbohydrate.

98. The method of claim 97 wherein the carrier is water soluble.

99. The method in claim 97 wherein the carbohydrate is a non starch polysaccharide selected from the group consisting of pectin, inulin, cellulose, hemicellulose, oligosaccharides and gums.

100. The method as in claim 99 wherein the carbohydrate is a pectin selected from the group consisting of high, medium and low methoxylated pectins and high, medium and low gel strength pectins and pectins derived from oranges, lemons or apples.

101. The method in claim 99 wherein the carbohydrate is a cellulose selected from the group consisting of microcrystalline cellulose, methyl cellulose, hydroxypropylmethyl cellulose and carboxymethyl cellulose.

102. The method in claim 99 wherein the carbohydrate is an oligosaccharide selected from the group consisting of fructooligosaccharides, galactooligosaccharides, and maltodextrins.

103. The method of claim 99 wherein the carbohydrate is a gum selected from the group consisting of guar, arabic, xantham, tragacanth, locust bean and psyllium.

104. The method of claim 97 wherein the carbohydrate is a starch.

105. The method of claim 104 wherein the starch is a starch digestible in the small intestine.

106. The method as in claim 104 wherein the starch is a starch resistant to digestion in the small intestine.

107. The method as in claim 103 wherein the starch is a native starch.

108. The method as in claim 107 where the native starch is derived from a material selected from the group consisting of wheat, potato, tapioca, maize, rice and oat.

109. The method as in claim 103 wherein the starch is a modified starch.

110. The method as in claim 109 wherein the starch is modified through the use of any one or more of the following, heat/and/or moisture, physically, enzymatically, chemical hydrolysis, esterification, oxidation, cross bonding with difunctional reagents, and carboxymethylation.

111. The method as in claim 95 wherein the bond is either an ester bond or an amide bond.

112. The method as in claim 96 wherein the SCFA is selected from the group consisting of acetate, propionate, butyrate, and branched or modified derivatives thereof.

113. The method as in claim 96 wherein the SCFA is acetate.

114. The method as in claim 96 wherein the SCFA is propionate.

115. The method as in claim 96 wherein the SCFA is butyrate.

116. The method as in claim 97 wherein the degree of substitution ranges from 0.05 acyl group per saccharide unit to 2 acyl groups per saccharide unit.

117. The method as in claim 97 wherein the degree of substitution ranges from 0.1 acyl groups per saccharide unit to 0.5 acyl group per saccharide unit.

118. An agent comprising for delivering a fatty acid to the colon, said agent comprising a carrier covalently bonded to the fatty acid by a bond that is hydrolysible in the colon to give free acid, made according to the method of any one of claims 96 to 117.

* * * * *